United States Patent
Temtsin Krayz et al.

(10) Patent No.: US 9,254,268 B2
(45) Date of Patent: Feb. 9, 2016

(54) COMPOSITIONS COMPRISING LIPOPHILIC ACTIVE COMPOUNDS AND METHOD FOR THEIR PREPARATION

(75) Inventors: Galia Temtsin Krayz, Ashdod (IL); Maryana Averbuch, Ashdod (IL); Ilya Zelkind, Ofakim (IL); Larisa Gitis, Holon (IL)

(73) Assignee: SOLUBEST LTD., Ness Ziona (IL)

( * ) Notice: Subject to any disclaimer, the term of this patent is extended or adjusted under 35 U.S.C. 154(b) by 657 days.

(21) Appl. No.: 12/238,424

(22) Filed: Sep. 25, 2008

(65) Prior Publication Data

US 2009/0098200 A1  Apr. 16, 2009

Related U.S. Application Data

(60) Provisional application No. 60/975,066, filed on Sep. 25, 2007, provisional application No. 60/975,045, filed on Sep. 25, 2007.

(51) Int. Cl.
| | |
|---|---|
| A61K 9/14 | (2006.01) |
| A61K 9/16 | (2006.01) |
| A61K 9/00 | (2006.01) |
| A61K 9/20 | (2006.01) |
| A61K 9/24 | (2006.01) |
| A61K 9/50 | (2006.01) |
| A61K 31/192 | (2006.01) |

(52) U.S. Cl.
CPC ............ *A61K 9/1652* (2013.01); *A61K 9/0095* (2013.01); *A61K 9/1641* (2013.01); *A61K 9/209* (2013.01); *A61K 9/2018* (2013.01); *A61K 9/2077* (2013.01); *A61K 9/5084* (2013.01); *A61K 31/192* (2013.01)

(58) Field of Classification Search
None
See application file for complete search history.

(56) References Cited

U.S. PATENT DOCUMENTS

| | | | |
|---|---|---|---|
| 4,880,585 A | 11/1989 | Klimesch et al. | |
| 4,961,890 A | 10/1990 | Boyer | |
| 5,145,684 A | 9/1992 | Liversidge et al. | |
| 5,456,923 A | 10/1995 | Nakamichi et al. | |
| 6,074,670 A | 6/2000 | Stamm et al. | |
| 6,221,399 B1 | 4/2001 | Rolfes et al. | |
| 6,254,889 B1 | 7/2001 | Kigoshi et al. | |
| 6,277,405 B1 | 8/2001 | Stamm et al. | |
| 6,337,092 B1 | 1/2002 | Khan et al. | |
| 6,368,622 B2 | 4/2002 | Chen et al. | |
| 6,387,401 B2 | 5/2002 | Rosenberg et al. | |
| 6,395,300 B1 * | 5/2002 | Straub et al. | 424/489 |
| 6,589,522 B1 | 7/2003 | Galler et al. | |
| 6,599,528 B1 | 7/2003 | Rosenberg et al. | |
| 6,652,881 B2 | 11/2003 | Stamm et al. | |
| 6,706,283 B1 | 3/2004 | Appel et al. | |
| 6,730,322 B1 * | 5/2004 | Bernstein et al. | 424/486 |
| 6,878,693 B2 | 4/2005 | Goldshtein | |
| 6,884,433 B2 | 4/2005 | Yamashita et al. | |
| 7,037,529 B2 | 5/2006 | Stamm et al. | |
| 7,041,319 B2 | 5/2006 | Stamm et al. | |
| 7,081,450 B2 | 7/2006 | Goldshtein | |
| 7,101,576 B2 | 9/2006 | Hovey et al. | |
| 7,569,612 B1 * | 8/2009 | Arnold et al. | 514/687 |
| 2001/0006662 A1 | 7/2001 | Krill et al. | |
| 2002/0009494 A1 | 1/2002 | Curatolo et al. | |
| 2002/0034546 A1 | 3/2002 | Ullah et al. | |
| 2003/0068366 A1 * | 4/2003 | Chungi et al. | 424/452 |
| 2003/0104063 A1 | 6/2003 | Babcock et al. | |
| 2003/0224058 A1 | 12/2003 | Ryde et al. | |
| 2003/0228358 A1 | 12/2003 | Perlman et al. | |
| 2004/0013697 A1 | 1/2004 | Berndl et al. | |
| 2004/0052847 A1 | 3/2004 | Namburi et al. | |
| 2004/0058009 A1 | 3/2004 | Ryde et al. | |
| 2004/0087656 A1 | 5/2004 | Ryde et al. | |
| 2004/0091535 A1 * | 5/2004 | Vachon | A61K 9/145 424/471 |
| 2004/0141925 A1 | 7/2004 | Bosch et al. | |
| 2004/0198645 A1 | 10/2004 | Ambuhl et al. | |
| 2005/0096391 A1 | 5/2005 | Holm et al. | |
| 2005/0191359 A1 | 9/2005 | Goldshtein et al. | |
| 2005/0276974 A1 | 12/2005 | Ryde et al. | |
| 2006/0062809 A1 | 3/2006 | Six et al. | |
| 2006/0068015 A1 | 3/2006 | Holm et al. | |
| 2006/0110444 A1 | 5/2006 | Holm et al. | |
| 2006/0141048 A1 | 6/2006 | Kipp et al. | |
| 2006/0159766 A1 | 7/2006 | Jenkins et al. | |
| 2006/0222707 A1 | 10/2006 | Lerner et al. | |
| 2006/0287352 A1 | 12/2006 | Holm et al. | |

(Continued)

FOREIGN PATENT DOCUMENTS

| | | |
|---|---|---|
| CA | 2111851 A1 | 1/1993 |
| EP | 1774971 A1 | 4/2007 |
| EP | 1834635 A1 | 9/2007 |
| WO | 92/18102 A1 | 10/1992 |
| WO | 00/72829 A1 | 12/2000 |
| WO | 03028700 A2 | 4/2003 |
| WO | 03/103640 A1 | 12/2003 |

(Continued)

OTHER PUBLICATIONS

Leuner et al., "Improving drug solubility for oral delivery using solid dispersions" European Journal of Pharmaceutics and Biopharmaceutics 50:47-60 (2000).

*Primary Examiner* — Susan Tran
(74) *Attorney, Agent, or Firm* — Browdy and Neimark, PLLC

(57) ABSTRACT

Compositions are provided comprising a lipophilic active compound, e.g., a human or veterinary drug or a nutraceutical, interwoven with a polymeric matrix formed by two or more polymers, wherein one of the polymers is an amphiphilic polymer and the other polymer is either an amphiphilic polymer with a different hydrophobic-hydrophilic balance or a hydrophilic polymer, and the active lipophilic compound has modified physicochemical properties. The composition forms colloidal nanodispersion upon contact with aqueous media.

72 Claims, 5 Drawing Sheets

(56) References Cited

U.S. PATENT DOCUMENTS

| | | |
|---|---|---|
| 2007/0009603 A1 | 1/2007 | Holm et al. |
| 2007/0020335 A1 * | 1/2007 | Chen et al. .................... 424/486 |
| 2007/0026062 A1 | 2/2007 | Holm et al. |
| 2007/0141143 A1 | 6/2007 | Smithey et al. |
| 2007/0141159 A1 | 6/2007 | Bosch et al. |
| 2007/0148232 A1 | 6/2007 | Crew et al. |

FOREIGN PATENT DOCUMENTS

| | | |
|---|---|---|
| WO | 2004/041250 A2 | 5/2004 |
| WO | 2004/069138 A2 | 8/2004 |
| WO | 2005061004 A1 | 7/2005 |
| WO | WO 2006037346 A1 * | 4/2006 |
| WO | 2006/060817 A1 | 6/2006 |
| WO | 2007141806 A1 | 12/2007 |

* cited by examiner

COMPOSITIONS COMPRISING LIPOPHILIC ACTIVE COMPOUNDS AND METHOD FOR THEIR PREPARATION

FIELD OF THE INVENTION

The present invention relates to compositions comprising lipophilic active compounds and polymers, and more particularly to pharmaceutical compositions comprising lipophilic drugs for oral administration.

BACKGROUND OF THE INVENTION

Lipophilic drug substances having low water solubility are a growing class of drugs with increasing applicability in a variety of therapeutic areas for a variety of pathologies. Many compounds approved for pharmaceutical use are lipophilic compounds with limited solubility and bioavailability. Relatively insoluble compounds, i.e., solubility in water of less than 200 µg/ml may show promising pharmaceutical activity, but their development as pharmaceuticals, particularly in oral dosage form, present a significant challenge to the pharmaceutical industry.

Among the main barriers for effective drug delivery are solubility and stability. To be absorbed in the human body, a compound has to be soluble in both water and fats (lipids). However, solubility in water is often associated with poor fat solubility and vice-versa.

Solubility and stability are, therefore, major obstacles hindering the development of therapeutic agents. Aqueous solubility is a necessary but frequently elusive property for formulations of the complex organic structures found in pharmaceuticals. Traditional formulation systems for very insoluble drugs have involved a combination of organic solvents, surfactants and extreme pH conditions. These formulations are often irritating to the patient and may cause adverse reactions. At times, these methods are inadequate for solubilizing enough of a quantity of a drug for a parenteral formulation.

Bioavailability refers to the degree to which a drug becomes available to the target tissue or any alternative in vivo target (i.e., receptors, tumors, etc.) after being administered to the body. Poor bioavailability is a significant problem encountered in the development of pharmaceutical compositions, particularly those containing an active ingredient that is poorly soluble in water. Poorly water-soluble drugs tend to be eliminated from the gastrointestinal tract before being absorbed into the circulation.

In order to increase the solubility of poorly soluble drugs, several techniques have been used such as (i) selection of more soluble polymorphs, hydrates or salts; (ii) addition of additives as surfactants to solubilize the drug; and (iii) use of particle size reduction (e.g., micronization) which increases the area of drug in contact with the medium, to accelerate dissolution. These techniques, however, were sometimes inadequate to provide satisfactory solubility.

More sophisticated solubilization approaches have been developed in recent years, based on; (i) a new generation of size reduction technology; (ii) advanced solubilizing agents that "drag" the insoluble drug into solution and increase the miscibility of the drug with aqueous media; and (iii) use of amorphous forms or eutectic mixtures to reduce the thermodynamic barriers to dissolution With regard to the size reduction, it is known that the rate of dissolution of a particulate drug can increase with increasing surface area, namely, decreasing particle size. It is generally accepted that water insoluble or poorly water-soluble drugs can be made more bioavailable when presented in the form of small particles. The new techniques for size reduction reduce the particle size to a much greater extent than ever previously seen; hence the micronization of the past has been replaced by new technologies that produce nanoparticles, which are up to 1000 times smaller. Above and beyond the dramatic increase in surface area seen with nanoparticles (and the consequent effects on the rate of dissolution), it has been suggested that the use of particles in the nanosize range may even increase the saturation solubility of a drug in an aqueous medium and allow local supersaturation.

Nanoparticles can be generated by many different means, such as size reduction by advanced milling techniques or by precipitation. However, after the formation of the drug nanoparticles, many of these techniques face a common problem: the tendency of very small drug particles to agglomerate together. Many of the inventions in the field focus on preventing this agglomeration, often by coating the nanoparticles A number of solubilization technologies for water-insoluble drugs exist such as nanosuspensions, nanoparticles, liposomes, cyclodextrins, dendrimers, micro- and nanoencapsulation, and solid dispersion, but each of these technologies has a number of significant disadvantages.

One of the methods employed to increase the surface area of particles and thus enhance the solubility of water-insoluble compounds in drug formulations is to make a solid dispersion of insoluble pharmaceutical substances in high molecular weight water-soluble polymeric matrices, which act as a solubility bridge between the insoluble compound and an aqueous medium (Christian Leuner and Jennifer Dressman, 2000, Improving drug solubility for oral delivery using solid dispersions, European Journal of Pharmaceutics and Biopharmaceutics, 50: 47-60). A solid dispersion always contains at least two components: a matrix and a drug. The matrix can be either amorphous or crystalline, and the drug can be dispersed within the matrix as a molecular dispersion or as nanosized crystals or as amorphous particles. It is currently not clear how the complex interactions between drug-matrix and aqueous solvent improve the solubility of the drug.

Solid dispersions are physico-chemically classified as eutectics, solid solutions, glass solutions, glass suspensions, amorphous precipitate in a glassy or crystalline carrier, complex formation and/or a combination of the different systems. With the proper choice of polymers it is possible to significantly increase the solubility of the drug substance as well. Although there are a few marketed drugs that have been formulated as solid dispersions, the major obstacle has been that they are insufficiently stable, and in order to be able to apply these dispersions widely in the pharmaceutical area significant stability improvements are needed.

Forming a stable mixture of polymer matrix and drug, which maximizes the dissolution properties of the drug when exposed to aqueous medium (GI fluid) and which is preferably as uniform as possible is the aim when preparing solid dispersions.

Solid dispersion dosage forms may be formed by solvent method, by spray drying, by spraying drug solution onto the carrier in a fluidized bed granulator, by melt extrusion, by melt fusion, twin-screw extruder, evaporation, curing, microwaving, milling, ultra sound, spinning by mechanical admixture such as by ball milling and by mechanical admixture at an elevated but non-melting temperature. See, for example, U.S. Pat. No. 4,880,585, U.S. Pat. No. 5,456,923, U.S. Pat. No. 6,254,889, U.S. Pat. No. 6,387,401, U.S. Pat. No. 6,706,283, U.S. Pat. No. 6,599,528, and US 2004/0013697.

The solvent method for the preparation of solid dispersions of poorly-soluble drugs involves the dissolution of the matrix material in a solvent. The drug is either suspended or dissolved in the matrix-solvent mixture and the solvent is then removed to leave a mixture of drug and matrix. Separation methods include precipitation, freeze-drying, vacuum drying or spray drying.

To dissolve the drug and the matrix in a common solvent is a considerable problem. If low drug concentrations and large amounts of solvent are used, the process of removing the solvent becomes expensive and impractical. Surfactants like Tween and solubilizing agents like cyclodextrins have been used, however this can lead to low drug loads and high concentrations of surfactants, which then change the properties of the matrix and which may be poorly-tolerated or even toxic. Suitable solvents may only be found in those regarded by the FDA as toxic, which renders them impractical for pharmaceutical use.

Thus, despite many years of research and development and despite its theoretical promise, solid dispersion approach has proved to be limited in its practical application. Its problems include: (i) lack of a scientific framework and the need to use trial and error—only a specific matrix developed for a specific drug; (ii) problems of scale up with the methods used; and (iii) problems with the physical and chemical stability of the drug-polymer matrix. The problems with matrix selection are due to the mutual incompatibility of the various requirements: low hygroscopicity, fast dissolution, stability and easy to manufacture. So for instance, a polar matrix, which aids dissolution, when combined with a lipophilic drug, is inherently prone to phase separation, a tendency that can be magnified if the polar matrix is also hygroscopic, which reduces stability. On the other hand, a stable matrix requires low molecular mobility (to prevent phase changes of the drug), this usually requires high molecular weight, which makes it difficult to find a common solvent for drug and polymer. However, if the matrix is made from a less polar polymer, in order to more easily find a common solvent, then the dissolution rate is impaired. It would be highly desirable to find the ideal matrix and a simple production process.

U.S. Pat. No. 5,145,684 discloses dispersible particles consisting essentially of a crystalline drug substance having a surface modifier adsorbed on the surface thereof in an amount sufficient to maintain an effective average particle size of less than about 400 nm and dispersions containing the particles exhibit unexpected bioavailability WO 2004/069138 discloses a process for preparing a solid dispersion pharmaceutical product containing a pharmaceutical active ingredient and a polymer, wherein the pharmaceutical active ingredient is relatively insoluble and has a lower melting point or glass transition point than the water soluble polymer of choice, comprising first liquefying or softening the active ingredient and then adding the polymer to produce a mixture of the liquefied or softened pharmaceutical active ingredient with the polymer, then allowing said liquefied or softened mixture to become liquefied throughout, then allowing said mixture to form a molecular dispersion of pharmaceutical active ingredient and polymer, and then solidifying said dispersion in order to create a solid dispersion. Preferred polymers are polyvinylpyrrolidone (PVP) and hydroxypropylmethylcellulose (HPMC). Also hydrophobic polymers and mixtures of polymers can be used. The pharmaceutical active ingredient is preferably first melted and then mixed with a water-soluble polymer.

U.S. Pat. No. 6,337,092 discloses pharmaceutical compositions comprising electrostatic and steric-stabilized sub-micron and micron-size stable microparticles of water-insoluble or poorly soluble drugs, the particles having phospholipid coated surfaces and being stabilized with a combination of a highly purified charged phospholipid surface modifier and a block copolymer of ethylene oxide and propylene oxide.

US 2002/009494 discloses a composition comprising spray dried solid dispersions comprising a sparingly soluble drug and hydroxypropylmethylcellulose acetate succinate (HPMCAS) that provide increased aqueous solubility and/or bioavailability in a use environment.

US 2004/0052847 discloses a method of manufacturing an active agent oral dosage form, said method comprising the steps of: providing a single phase working solution comprising an active agent, water, a water-soluble polymer and a solvent, said solvent selected from the group consisting of alcohol, acetone, and mixtures thereof; providing core particles formed from a pharmaceutically acceptable material; combining said working solution with said particles to produce active agent-coated particles; drying said active agent-coated particles; and forming said dried particles into an oral dosage form.

Numerous patents/patent applications deal with the preparation of compositions comprising fenofibrate, a lipophilic drug useful for treating hyperlipidemia, particularly to reduce cholesterol and triglyceride levels in patients at risk of cardiovascular disease. Thus, several compositions have been developed or proposed to improve the solubility and bioavailability of fenofibrate and to reduce the food effect of blood levels of the active drug.

U.S. Pat. No. 4,961,890 discloses a process for preparing a controlled release formulation containing fenofibrate in an intermediate layer in the form of crystalline microparticles included within pores of an inert matrix. Sheu M T et al. (Int. J. Pharm. 103:137-146, 1994) reported that a dispersion of fenofibrate in polyvinylpyrrolydone (PVP) still maintains the same crystalline form of the drug itself. Palmieri G F et al. (Pharma Sciences 6:188-194, 1996) reported that a dispersion of crystalline fenofibrate could be prepared in PEG 4000.

U.S. Pat. No. 6,074,670, U.S. Pat. No. 6,277,405, U.S. Pat. No. 6,589,522 and U.S. Pat. No. 6,652,881 (assigned to Laboratoires Fournier) disclose an immediate-release fenofibrate composition comprising an inert hydrosoluble carrier covered with at least one layer containing a fenofibrate active ingredient in a micronized form having a size less than 20 µm, a hydrophilic polymer and a surfactant, and optionally one or several outer phase(s) or layer(s).

U.S. Pat. No. 6,368,622 (assigned to Abbott Laboratories) discloses a process for preparing a solid formulation of a fibrate, particularly fenofibrate, exhibiting more rapid dissolution, comprising forming a mixture of the fibrate with a solid surfactant and granulating the mixture by melting, mixing, and congealing, then optionally forming a finished dosage form. U.S. Pat. No. 6,465,011 (Abbott Laboratories) discloses a composition comprising a fibrate, particularly fenofibrate, dissolved in a hydrophilic, amorphous polymer carrier in which said fibrate is present as a metastable, amorphous phase. WO 00/72829 (Abbott Laboratories) discloses a composition for lipid-regulating drugs including fenofibrate comprising the active drug and excipient in a eutectic mixture.

U.S. Pat. No. 7,037,529 and U.S. Pat. No. 7,041,319 (assigned to Laboratoires Fournier) disclose fenofibrate compositions comprising granulates, wherein the granulates comprise inert carrier particles coated with an admixture comprising at least one hydrophilic polymer, micronized fenofibrate and optionally a surfactant and wherein the composition has a high dissolution rate in solutions of surfactants.

US 2006/0222707, assigned to Teva Pharmaceuticals, discloses a pharmaceutical composition comprising a fibrate drug, particularly fenofibrate, in intimate association with a surfactant mixture comprising PEG 6000 and Poloxamer 407. The composition is prepared by a process comprising: (a) providing melted menthol; (b) mixing melted menthol with the fibrate drug and a surfactant mixture comprising PEG 6000 and Poloxamer 407 to dissolve at least part of the fibrate drug and the surfactant mixture, and removing the menthol via sublimation.

WO 2006/060817 (Abbott Laboratories) discloses an oral pharmaceutical composition comprising fenofibrate and at least one pharmaceutically acceptable polymer and, optionally, at least one pharmaceutically acceptable surfactant. The composition can be in the form of a solid dispersion that forms a suspension upon in contact with an aqueous medium. The suspension comprises crystalline and/or amorphous fenofibrate particles of various particle sizes. The solid dispersions are prepared by a melt-extrusion method.

US 2003/0224058 (now U.S. Pat. No. 7,276,249), US 2004/0058009, US 2004/0087656 and US 2005/0276974, US 2006/0110444, US 2006/0222707 and WO 2004/041250, (assigned to Elan Pharma and Fournier Laboratories) disclose nanoparticulate compositions comprising a fibrate, preferably fenofibrate, and at least one surface stabilizer adsorbed on the surface of the fibrate particles. The fenofibrate particles have an effective average particle size of less than about 2000 nm and are obtained by milling, homogenization or precipitation techniques and then coating by the surface stabilizers to prevent aggregation. The formulations containing fenofibrate as either a nanoparticulate or a molecular dispersion in a solid dosage form eliminate the food effect associated with fenofibrate.

Some more recent publications disclose methods and compositions comprising low-solubility drugs and two polymers.

US 2003/0104063 discloses a pharmaceutical composition comprising: (a) a solid dispersion comprising a low-solubility drug and a matrix (which can be formed by one or more polymers), wherein at least a major portion of said drug in said dispersion is amorphous; and (b) a concentration-enhancing polymer which further improves solubility in the use environment and may not be part of the drug/matrix dispersion, instead it is mixed in with the drug/matrix particles or given separately.

US 2003/0228358 discloses a pharmaceutical composition comprising a solid amorphous dispersion of a low-solubility drug and a concentration-enhancing polymer, administered together with a lipophilic microphase-forming material, which may be present as part of the solid amorphous dispersion or mixed in with the dispersion or even given separately with the dispersion.

US 2007/0141143 discloses a solid composition comprising a plurality of particles, said particles comprising a low-solubility drug and a poloxamer, at least a substantial portion of said drug in said particles being amorphous and being in intimate contact with said poloxamer in said particles, and further optionally comprising a concentration-enhancing polymer.

US 2007/0148232 discloses solid compositions with improved physical stability comprising an amorphous, low-solubility drug, a poloxamer, and a stabilizing polymer, preferably a cellulosic polymer. The compositions are prepared by a solvent-based process and spray-drying and provide good physical stability during storage and concentration enhancement of dissolved drug when administered to an aqueous environment.

Statins are currently among the most therapeutically effective drugs available for reducing the level of LDL in the blood stream of a patient at risk for cardiovascular disease. Statins are also known to raise HDL cholesterol levels and decrease total triglyceride levels. The main statins currently used in therapeutics are: pravastatin, simvastatin, lovastatin, fluvastatin, atorvastatin and rosuvastatin.

US 2001/0006662 discloses a composition comprising a lipid-regulating agent, e.g. atorvastatin or pravastatin, dissolved or dispersed in a hydrophilic, amorphous polymer in which said lipid-regulating agent is present as a meta-stable, amorphous phase. WO 03/103640 describes a nanoparticulate composition (effective average particle size less than about 2000 nm) comprising statin such as lovastatin or simvastatin including surface stabilizer or combinations of statin and other cholesterol lowering agents. US 2002/0034546 discloses a pharmaceutical composition which is useful for cholesterol lowering and reduction of the risk of myocardial infarction, which includes a statin, such as pravastatin, lovastatin, simvastatin, atorvastatin, cerivastatin or fluvastatin, in combination with aspirin, in a manner to minimize interaction of aspirin with the statin and to minimize side effects of aspirin.

Compositions comprising fenofibrate and a statin have been described. US 2005/0096391 discloses a particulate material comprising fenofibrate and rosuvastatin in a hydrophobic, a hydrophilic or a water-miscible vehicle. US 2006/0068015 and US 2007/0009603 discloses pharmaceutical compositions in particulate form or in solid dosage forms comprising a combination of fenofibrate and atorvastatin, which are manufactured without any need of addition of water or aqueous medium and comprise at least 80% of the active substances fenofibrate and atorvastatin in dissolved form, or, optionally, atorvastatin in micronized form, in order to ensure suitable bioavailability.

Compositions comprising tacrolimus, an immunosuppressive lipophilic drug used mainly after allogenic organ transplant to prevent organ rejection, have been described. US 2006/0159766 is directed to nanoparticulate tacrolimus compositions comprising tacrolimus particles having an effective average particle size of less than about 2000 nm and at least one surface stabilizer. US 2006/0287352 discloses a modified release composition comprising tacrolimus that may be coated with an enteric coating and/or may comprise a solid dispersion or a solid solution of tacrolimus in a hydrophilic or water-miscible vehicle and one or more modifying release agents; and/or may comprise a solid dispersion or a solid solution of tacrolimus in an amphiphilic or hydrophobic vehicle and optionally one or more modifying release agents. U.S. Pat. No. 6,884,433 describes sustained-release formulation comprising a solid dispersion composition, wherein the solid dispersion composition comprises tacrolimus or its hydrate, in a mixture comprising a water-soluble polymer and a water-insoluble polymer, and an excipient.

US 2004/0198645 discloses a solid pharmaceutical composition comprising a poorly water-soluble drug (e.g. cyclosporin A), a polymer which is solid at room temperature, and a surfactant which is solid at room temperature and which has a HLB value of between 8 and 17.

U.S. Pat. No. 7,101,576 discloses a megestrol acetate formulation comprising megestrol particles having an effective average particle size of less than about 2000 nm, and at least one surface stabilizer (e.g., polymer) associated with the surface of the particles.

US 20060062809 describes solid dispersions comprising a poorly soluble bioactive compound (e.g. itraconazole) dispersed and characterized in a polymer matrix which may comprise more than one polymer. US 2005/0191359 of the present applicant discloses a hydrophilic dispersion of nano-sized particles comprising an active compound selected from a macrolide antibiotic, donepezil hydrochloride, an azole compound (e.g. itraconazole) and a taxane; and an amphiphilic polymer which wraps said active compound in a non-crystalline manner to form a nano-sized molecular entity in which no valent bonds are formed.

U.S. Pat. No. 6,221,399 describes a method of making a solid interpolymer complex for use as a controlled release matrix for a controlled release product for oral administration, from a first polymer and one or more second complementary polymers capable of complexing with the first polymer to form the interpolymer complex, wherein one of the first polymer or the second complementary polymer is a synthetic polymer, including the steps of: (i) dissolving the first polymer in a solvent; (ii) dissolving the second complementary polymer in a solvent therefor, the solvent for said second polymer being the same as that used for step (i) or different; (iii) the solvent in at least one of step (i) or (ii) functioning as a complexation inhibitor or adding a complexation inhibitor to the solution of step (i) or the solution of step (ii), so that a complexation inhibitor is present to prevent the interpolymer complex from precipitating from solution prior to step (vi); (iv) mixing together the solutions of steps (i) and (ii); (v) if necessary, adjusting the pH of the mixture of step (iv) to insure the desired complexation when solvent is removed while avoiding precipitation of the complex; and (vi) spraying the resulting solution into a vessel to remove solvent, including any complexation inhibitor added thereto, to enable the polymers to complex and thereby produce solid particles of said complex.

US 2006/0062809 describes solid dispersions comprising a poorly soluble bioactive compound dispersed in a polymer matrix comprising more than one polymer, characterized in that a first polymer allows a homogenous or molecular dispersion of the bioactive compound in the polymer matrix, while a second polymer has a dissolution profile associated with the creation of a micro-environment enhancing the dissolution of the bioactive compound in an aqueous environment.

US 2007/0026062 describes a solid dosage form comprising a solid dispersion or solid solution of a fibrate selected from gemfibrozil, fenofibrate, bezafibrate, clofibrate, ciprofibrate and active metabolites and analogues thereof including any relevant fibric acid such as fenofibric acid in a vehicle, which is hydrophobic, hydrophilic or water-miscible, wherein the therapeutic effect of the solid dosage form in a patient is essentially independent of whether the solid dosage form is administered to the patient in fed or fasted state.

Although numerous patents/patent applications propose different methods for the preparation of formulations of lipophilic agents, there is still a need for such formulations exhibiting immediate release and improved bioavailability and for methods for their preparation that are more efficient and less complex than the available methods.

SUMMARY OF THE INVENTION

The present invention provides a solid composition comprising at least one lipophilic active compound, in which the at least one lipophilic active compound has modified physico-chemical properties in comparison to the same at least one lipophilic active compound used as the starting product for preparation of the composition. This composition is stable and upon contact with aqueous media forms a colloidal nanodispersion.

In the composition of the invention, the at least one lipophilic active compound interacts and is interwoven with a polymeric entity/matrix formed by two or more polymers (herein in the specification designated "polymer matrix" or "polymeric entity") possessing a hydrophobic-hydrophilic range. This polymeric matrix is not crosslinked and no covalent interaction occurs between the two or more polymers that form the polymeric matrix and between the two or more polymers and the at least one lipophilic active compound.

The interaction between the lipophilic active compound and the two or more polymers gives rise to self-assembly of a complex, herein designated "polymers-lipophilic active compound complex", in which the lipophilic active compound is fixated within the polymer matrix/polymeric entity that surrounds it, but is not linked to the polymers by any covalent bond. In the polymers-lipophilic active compound complex, the lipophilic active compound possesses modified physico-chemical properties, more specifically modified thermal properties, which are characterized by either decreased enthalpy of melting or both decreased enthalpy of melting and decreased temperature of melting, as compared to the bulk active compound, e.g., crystalline active compound, used for the preparation of the composition.

Thus, the present invention relates to a solid composition that forms a colloidal nanodispersion upon contact with aqueous media, said composition comprising at least one lipophilic active compound and two or more polymers, in which composition the at least one lipophilic active compound is interwoven with a polymeric matrix formed by the two or more polymers, wherein at least one of the two or more polymers is an amphiphilic polymer and at least another of the two or more polymers is either a hydrophilic polymer or an amphiphilic polymer with a hydrophobic-hydrophilic balance different from the first amphiphilic polymer, and each of the at least one lipophilic active compounds has modified physico-chemical properties as compared to the same lipophilic active compound used as the starting product for the preparation of the composition.

In one embodiment, the at least one lipophilic active compound in the composition has modified thermal properties, characterized by decreased enthalpy of melting ($\Delta H_{melt}$) as compared to the bulk active compound, e.g., crystalline active compound, used for the preparation of the composition. In another embodiment, the modified thermal properties are characterized by both decreased enthalpy of melting ($\Delta H_{melt}$) and decreased temperature of melting ($T_{melt}$), as compared to the bulk active compound, e.g., crystalline active compound, used for the preparation of the composition.

The interaction between the lipophilic active compound and the two or more polymers results in creation of a hydrophobic-hydrophilic gradient or range that enables formation of a colloidal nanodispersion upon contact of the composition with aqueous media, facilitating fast release of the lipophilic active compound and ensuring its high bioavailability. The amphiphilic polymer is the gradient inducer, namely, it forms the "bridge" between the hydrophobic and the hydrophilic segments in the lipophilic drug-polymers complex and induces the formation of the hydrophobic-hydrophilic gradient.

The lipophilic active compound may be a lipophilic drug, both for human and veterinary use, or a nutraceutical. In one preferred embodiment, the active compound is a lipophilic drug and the composition of the invention is a pharmaceutical composition, preferably for oral administration. In another embodiment, the lipophilic compound is a veterinary drug, and the composition is a veterinary composition. In a further embodiment, the lipophilic compound is a nutraceutical and the composition is a nutraceutical composition.

In one preferred embodiment, two polymers, one of which must be an amphiphilic polymer, form the polymeric entity. In one embodiment, a first polymer is an amphiphilic polymer and the second polymer is an amphiphilic polymer with different hydrophobic-hydrophilic balance, for example with a higher degree of hydrophilicity than the first one. In another more preferred embodiment, the first polymer is an amphiphilic polymer and the second polymer is a hydrophilic polymer.

In another preferred embodiment, three polymers, one of which must be an amphiphilic polymer, form the polymeric entity. In one embodiment, the three polymers are amphiphilic polymers with different hydrophobic-hydrophilic balance. In a more preferred embodiment, two of the polymers are amphiphilic polymers of different hydrophilicities and the third polymer is a hydrophilic polymer.

The present invention further relates to a method for the preparation of a composition of the invention comprising the steps:

(i) preparing a clear and homogeneous solution of the two or more polymers and the at least one lipophilic active compound in a mixture of water and organic solvent; and (ii) drying the polymers-lipophilic active compound complex clear solution of (i) to form a dry powder.

The dry powder composition obtained by the method of the invention contains the at least one lipophilic active compound fixated within the polymeric entity possessing a hydrophilic-hydrophobic gradient. The thus fixated lipophilic active compound is characterized by decreased enthalpy of melting or by decrease of both enthalpy of melting and temperature of melting of the lipophilic active compound as compared with the bulk lipophilic active compound used as the starting product for preparation of the composition. Upon contact with water or with aqueous media, e.g., biological fluids, the powder composition is converted into a colloidal dispersion with particles size in the nanoscale range.

The compositions of the invention are stable for at least 12 months when stored at 25° C. and 60% RH. The stored compositions do not exhibit any changes in their chemical or physicochemical properties such as formation of colloidal nanodispersion upon contact with aqueous media and decreased enthalpy of melting and decreased temperature of melting as the initial composition.

Another advantage of the compositions of the invention is the possibility of designing the composition such that a lipophilic drug will be released either in the gut or in the intestine. Thus, when the lipophilic active compound is a lipophilic drug, the polymers can be selected such that the drug release may be pH dependent so that the lipophilic drug will be released either in the gut or in the intestine. Thus, in a more preferred embodiment of the invention, the lipophilic drug powder forms colloidal nanodispersion upon contact with aqueous media or biological fluids with pH 6-8 that corresponds to the pH of intestinal fluids.

The present invention also relates to pharmaceutical compositions comprising at least one lipophilic drug interwoven with, and fixated within, the polymeric entity having a hydrophobic-hydrophilic gradient and may further comprise one or more pharmaceutically acceptable carriers and/or excipients, preferably solid carriers and/or excipients. The composition can be further processed and formulated into dosage forms for oral administration such as, but not limited to, capsules, tablets, beads, grains, pills, granulates, granules, powder, pellets, sachets, troches, oral suspensions and aerosol. In one more preferred embodiment, the pharmaceutical composition of the invention is formulated into tablets.

The pharmaceutical composition of the invention may comprise a sole lipophilic drug or a combination of more than one, preferably two, drugs, in which one of the drugs is lipophilic and the other may be lipophilic or not.

The tablets of the invention disintegrate in aqueous media or biological fluids with formation of colloidal nanodispersion comprising the lipophilic drug. These nanodispersions are reversible: they can be dried and redispersed or diluted while keeping the same properties of the lipophilic drug.

The collective properties of the lipophilic drug composition of the invention including the thermal behavior, release, bioavailability, dispersability and dissolution are stable and reproducible.

DETAILED DESCRIPTION OF THE INVENTION

Figure 1:
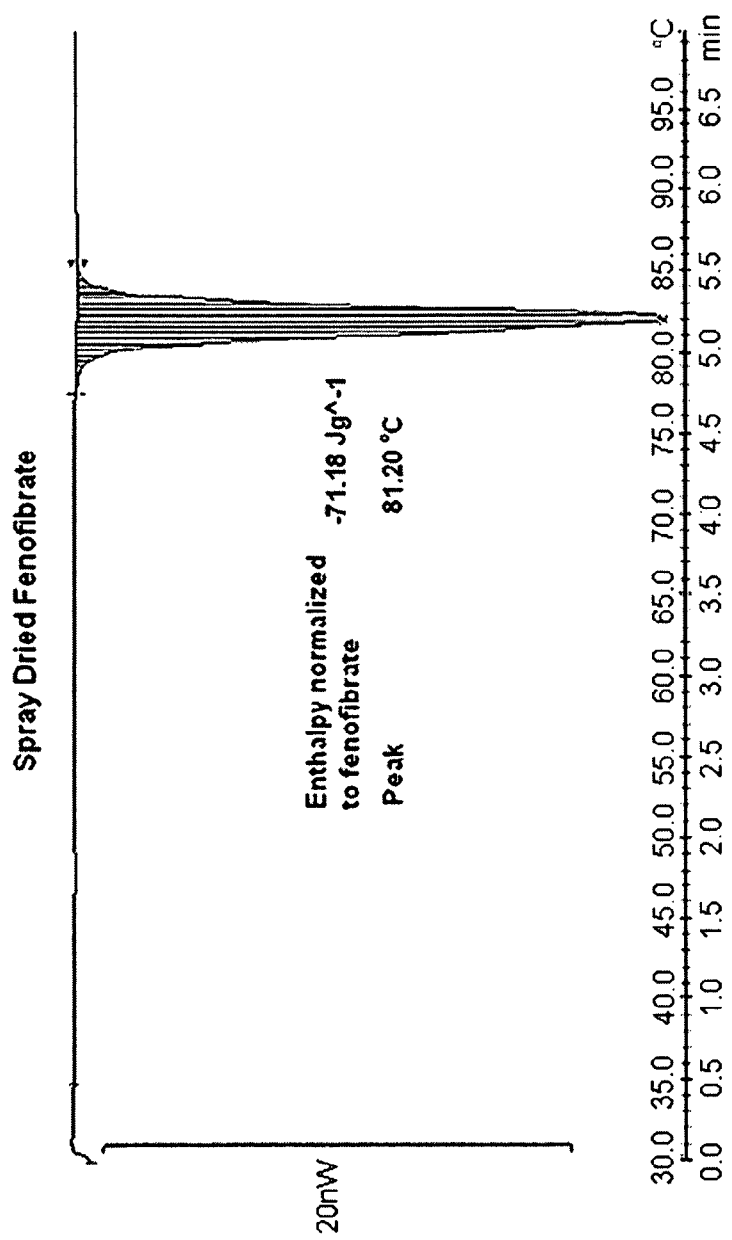
FIG. 1 depicts the Differential Scanning Calorimetry (DSC) thermogram of spray-dried fenofibrate alone (Example 1) as shown in Table 3 (Example 11).

As described in the Background of the Invention section hereinbefore, the Applicant of the present application, Solubest Ltd., has developed a basic technology described in U.S. Pat. No. 6,878,693 and U.S. Pat. No. 7,081,450 for the solubilization and improved bioavailability of lipophilic and hydrophilic active compounds in the form of nano-sized particles, wherein said active compound is surrounded by and entrapped within an amphiphilic polymer, to form a water-soluble nano-sized entity in which non-valent bonds are formed between said active compound and said amphiphilic polymer such that said bonds fixate said active compound within said polymer, in which nano-sized entity the active compound is in the amorphous or partially crystalline state and wherein said amphiphilic polymer does not form rigid matrices nor cross-linked polymers.

Contrary to the former concept, in accordance with the present invention the lipophilic active compound is interwoven with a polymeric entity formed by two or more polymers instead of a sole polymer, thus forming a polymers-lipophilic active compound complex system with a hydrophobic-hydrophilic gradient that enables formation of colloidal nanodispersion upon contact with aqueous media.

As used herein in the specification, the terms "polymeric matrix" or "polymeric entity", used interchangeably, refer to a non-crosslinked matrix or entity formed by the two or more polymers in which no covalent bonds exist between the two or more polymers.

The terms "polymers-lipophilic active compound complex" or "lipophilic active compound-polymers complex", used herein interchangeably, refer to a complex formed by the two or more polymers and the at least one active compound by self-assembly, wherein the at least one active compound is wrapped within/interwoven with, and is fixated within, the polymeric entity formed by the two or more polymers, but is not linked to the polymers by any covalent bond, and exhibits modified physico-chemical properties as compared to the starting bulk active compound used for preparation of the composition. The two or more polymers and the at least one active compound are linked by non-covalent bonds that include electrostatic forces, Van der Waals forces and hydrogen bonds. The polymeric entity is not crosslinked and does not form rigid matrices. It should be noted that, unlike cyclodextrins or inclusion complexes or other "encapsulants", the complex of the present invention does not provide a ready-made cavity or any cavity at all, but rather the polymer carriers are "interwoven" with the active compound creating a hydrophobic-hydrophilic gradient, all this accomplished by a self assembly mechanism.

The terms "interwoven with" is used herein to denote the condition in which the lipophilic drug is positioned in intimate contact within the polymeric entity.

Thus, in a first aspect, the present invention provides a composition in which at least one lipophilic active compound is interwoven with a polymeric entity formed by two or more polymers, wherein at least one of the two or more polymers is an amphiphilic polymer and at least another of the two or more polymers is an amphiphilic polymer with a different hydrophobic-hydrophilic balance or a hydrophilic polymer, and the interaction between the lipophilic active compound and the two or more polymers results in modification of its physico-chemical properties and enables formation of a colloidal nanodispersion comprising the lipophilic active compound upon contact with aqueous media.

The term "nanodispersion" is used herein to denote a dispersion in which at least 70% of the particles have a size less than 2000 nm, preferably less than 1500 nm, more preferably less than 1000 nm.

As used herein, the term "hydrophobic-hydrophilic balance" of the amphiphilic polymer refers to the "balance of hydrophobic and hydrophilic segments in the amphiphilic polymer chain" and both terms may be used herein interchangeably.

The lipophilic active compounds that can be used in accordance with the present invention include biologically active compounds and imaging agents and, in particular, drugs for human and veterinary medicine, and nutraceutical or dietary supplements. They include lipophilic water-insoluble compounds having solubility less than 10 mg/ml, preferably less than about 1 mg/ml and even less than about 0.1 mg/ml.

Suitable lipophilic active substances according to the invention include, but are not limited to, lipophilic active compounds or a salt, isomer, ester, ether or other derivative thereof selected from acetylcholinesterase inhibitors, analgesics and nonsteroidal antiinflammatory agents, anthelminthics, antiacne agents, antianginal agents, antiarrhythmic agents, anti-asthma agents, antibacterial agents, anti-benign prostate hypertrophy agents, anticancer agents and immunosuppressants, anticoagulants, antidepressants, antidiabetics, antiemetics, antiepileptics, antifungal agents, antigout agents, antihypertensive agents, antiinflammatory agents, antimalarials, antimigraine agents, antimuscarinic agents, antineoplastic agents, antiobesity agents, antiosteoporosis agents, antiparkinsonian agents, antiproliferative, antiprotozoal agents, antithyroid agents, antitussive agent, anti-urinary incontinence agents, antiviral agents, anxiolytic agents, appetite suppressants, beta-blockers, cardiac inotropic agents, chemotherapeutic drugs, cognition enhancers, contraceptives, corticosteroids, Cox-2 inhibitors, diuretics, erectile dysfunction improvement agents, expectorants, gastrointestinal agents, histamine receptor antagonists, hypnotics, immunosuppressants, keratolytics, lipid regulating agents, leukotriene inhibitors, macrolides, muscle relaxants, neuroleptics, nutritional agents, opioid analgesics, protease inhibitors, sedatives, sex hormones, stimulants, vasodilators, essential fatty acids, non-essential fatty acids, proteins, peptides, sugars, vitamins, nutraceuticals, natural agents, or mixtures thereof.

A description of these classes of compounds and a listing of the species within each class may be found in Remingtons's The Science and Practice of Pharmacy, 20th Ed (2000). All these drug substances are commercially available and/or can be prepared by techniques known in the art.

Among the lipophilic active compounds for use in the invention are lipophilic drugs of the Biopharmaceutical Classification System (BCS) class II drugs, characterized by low solubility and high permeability, and class IV drugs, characterized by low solubility and low permeability.

Representative examples of lipophilic substances that can be used in accordance with the present invention include, but are not limited to, lipophilic active compounds or a salt, isomer, ester, ether or other derivative thereof selected from:

(i) acetylcholinesterase inhibitors selected from donepezil, tacrine, pyridostigmine;

(ii) analgesics and nonsteroidal antiinflammatory agents (NSAIA) selected from aloxiprin, auranofin, azapropazone, benorylate, capsaicin, celecoxib, diclofenac, diflunisal, etodolac, fenbufen, fenoprofen calcium, flurbiprofen, ibuprofen, indomethacin, ketoprofen, ketorolac, leflunomide, meclofenamic acid, mefenamic acid, nabumetone, naproxen, oxaprozin, oxyphenbutazone, phenylbutazone, piroxicam, rofecoxib, sulindac, tetrahydrocannabinol, tramadol and tromethamine, (iii) anthelminthics selected from albendazole, bephenium hydroxynaphthoate, cambendazole, dichlorophen, fenbendazole, ivermectin, mebendazole, oxamniquine, oxfendazole, oxantel embonate, praziquantel, pyrantel embonate and thiabendazole;

(iv) antiacne agents such as isotretinoin and tretinoin;

(iv) antianginal agents selected from amyl nitrate, glyceryl trinitrate (nitroglycerin), isosorbide dinitrate, isosorbide mononitrate, pentaerythritol tetranitrate, and ubidecarenone (coenzyme Q10);

(v) antiarrhythmic agents selected from amiodarone HCl, digoxin, disopyramide, flecamide acetate and quinidine sulfate;

(vi) anti-asthma agents selected from zileuton, zafirlukast, terbutaline sulfate, montelukast, and albuterol;

(vii) antibacterial agents, including antibiotics, selected from alatrofloxacin, azithromycin, aztreonum, baclofen, benzathine penicillin, cefixime, cefuraxime axetil, cinoxacin, ciprofloxacin HCl, clarithromycin, clofazimine, cloxacillin, demeclocycline, dirithromycin, doxycycline, erythromycin, ethionamide, furazolidone, grepafloxacin, imipenem, levofloxacin, lorefloxacin, moxifloxacin HCl, nalidixic acid, nitrofurantoin, norfloxacin, ofloxacin, phenoxymethyl penicillin, rifabutine, rifampicin, rifapentine, sparfloxacin, spiramycin, sulphabenzamide, sulphadoxine, sulphamerazine, sulphacetamide, sulphadiazine, sulphafurazole, sulpha-methoxazole, sulphapyridine, tetracycline, trimethoprim, trovafloxacin, and vancomycin;

(vii) anti-benign prostate hypertrophy (BPH) agents selected from alfuzosin, doxazosin, phenoxybenzamine, prazosin, terazosin and tamulosin;

(viii) anticancer agents and immunosuppressants selected from abarelix, aldesleukin, alemtuzumab, alitretinoin, all-trans retinoic acid (ATRA), altretamine, amifostine, amino-glutethimide, amsacrine, anastrozole, arsenic trioxide, asparaginase, azacitidine, azathioprine, BCG Live, bevacuzimab (avastin), bexarotene, bicalutamide, bisantrene, bleomycin, bortezomib, busulfan, calusterone, camptothecin, capecitabine, carboplatin, carmustine, celecoxib, cetuximab, chlorambucil, cisplatin, cladribine, clofarabine, cyclophosphamide, cyclosporin, cytarabine, dacarbazine, dactinomycin, darbepoetin alfa, daunorubicin, denileukin, dexrazoxane, docetaxel, doxorubicin (neutral), doxorubicin HCl, dromostanolone propionate, ellipticine, enlimomab, estramustine, epirubicin, epoetin alfa, erlotinib, estramustine, etoposide, exemestane, filgrastim, floxuridine fludarabine, fulvestrant, gefitinib, gemcitabine, gemtuzumab, goserelin acetate, histrelin acetate, hydroxyurea, ibritumomab, idarubicin, ifosfamide, imatinib mesylate, interferon alfa-2a, interferon alfa-2b, irinotecan, lenalidomide, letrozole, leucovorin, leuprolide acetate, levamisole, lomustine, megestrol acetate, melphalan, mercaptopurine, mesna, methotrexate, methoxsalen, mitomycin C, mitotane, mitoxantrone, mofetil mycophenolate, nandrolone, nelarabine, nilutamide, nofetumomab, oprelvekin, oxaliplatin, paclitaxel, palifermin, pamidronate, pegademase, pegaspargase, pegfilgrastim, pemetrexed disodium, pentostatin, pipobroman, plicamycin, porfimer sodium, procarbazine, quinacrine, rasburicase, rituximab, sargramostim, sirolimus, sorafenib, streptozocin, sunitinib maleate, tacrolimus, tamoxifen citrate, temozolomide, teniposide, testolactone, thioguanine, thiotepa, topotecan, toremifene, tositumomab, trastuzumab, tretinoin, uracil mustard, valrubicin, vinblastine, vincristine, vinorelbine, zoledronate, and zoledronic acid;

(ix) anticoagulants selected from cilostazol, clopidogrel, dicumarol, dipyridamole, nicoumalone, oprelvekin, phenindione, ticlopidine, and tirofiban;

(x) antidepressants selected from amoxapine, bupropion, citalopram, clomipramine, fluoxetine HCl, maprotiline HCl, mianserin HCl, nortriptyline HCl, paroxetine HCl, sertraline HCl, trazodone HCl, trimipramine maleate, and venlafaxine HCl;

(xi) antidiabetics selected from acetohexamide, chlorpropamide, glibenclamide, gliclazide, glipizide, glimepiride, glyburide, miglitol, pioglitazone, repaglinide, rosiglitazone, tolazamide, tolbutamide and troglitazone;

(xii) antiepileptics selected from beclamide, carbamazepine, clonazepam, thotoin, felbamate, fosphenyloin sodium, lamotrigine, methoin, methsuximide, methylphenobarbitone, oxcarbazepine, paramethadione, phenacemide, phenol barbitone, phenyloin, phensuximide, primidone, sulthiame, tiagabine HCl, topiramate, valproic acid, and vigabatrin;

(xiii) antifungal agents selected from amphotericin, butenafine HCl, butoconazole nitrate, clotrimazole, econazole nitrate, fluconazole, flucytosine, griseofulvin, itraconazole, ketoconazole, miconazole, natamycin, nystatin, sulconazole nitrate, oxiconazole, terbinafine HCl, terconazole, tioconazole and undecenoic acid;

(xiv) antigout agents selected from allopurinol, probenecid and sulphinpyrazone;

(xv) antihypertensive agents selected from amlodipine, benidipine, benezepril, candesartan, captopril, darodipine, dilitazem HCl, diazoxide, doxazosin HCl, enalapril, eposartan, losartan mesylate, felodipine, fenoldopam, fosenopril, guanabenz acetate, irbesartan, isradipine, lisinopril, minoxidil, nicardipine HCl, nifedipine, nimodipine, nisoldipine, phenoxybenzamine HCl, prazosin HCl, quinapril, reserpine, terazosin HCl, telmisartan, and valsartan;

(xvi) antimalarial agents selected from amodiaquine, chloroquine, chlorproguanil HCl, halofantrine HCl, mefloquine HCl, proguanil HCl, pyrimethamine and quinine sulfate;

(xvii) antimigraine agents selected from dihydroergotamine mesylate, ergotamine tartrate, frovatriptan, methysergide maleate, naratriptan HCl, pizotifen maleate, rizatriptan benzoate, sumatriptan succinate, and zolmitriptan;

(xviii) antimuscarinic agents selected from atropine, benzhexol HCl, biperiden, ethopropazine HCl, hyoscyamine, mepenzolate bromide, oxyphencyclimine HCl and tropic amide (xix) antiparkinsonian agents selected from bromocriptine mesylate, lysuride maleate, pramipexole, ropinirole HCl, and tolcapone;

(xx) antiprotozoal agents selected from atovaquone, benznidazole, clioquinol, decoquinate, diiodohydroxyquinoline, diloxamide furoate, dinitolmide, furazolidone, metronidazole, nimorazole, nitrofurazone, ornidazole and tinidazole;

(xxi) antithyroid agents selected from carbimazole and propylthiouracil;

(xxii) antitussive agent such as benzonatate;

(xxiii) antiviral agents selected from abacavir, amprenavir, delavirdine, efavirenz, indinavir, lamivudine, nelfinavir, nevirapine, ritonavir, saquinavir, and stavudine;

(xxiv) anxiolytics, sedatives, hypnotics and neuroleptics selected from alprazolam, amylobarbitone, barbitone, bentazepam, bromazepam, bromperidol, brotizolam, butobarbitone, carbromal, chlordiazepoxide, chlormethiazole, chlorpromazine, chlorprothixene, clonazepam, clobazam, clotiazepam, clozapine, diazepam, droperidol, ethinamate, flunanisone, flunitrazepam, triflupromazine, flupenthixol decanoate, fluphenthixol decanoate, flurazepam, gabapentin, haloperidol, lorazepam, lormetazepam, medazepam, meprobamate, mesoridazine, methaqualone, methylphenidate, midazolam, molindone, nitrazepam, olanzapine, oxazepam, pentobarbitone, perphenazine pimozide, prochlorperazine, propofol, pseudoephedrine, quetiapine, risperidone, sertindole, sulpiride, temazepam, thioridazine, triazolam, zolpidem, and zopiclone;

(xxv) beta.-blockers selected from acebutolol, alprenolol, atenolol, labetalol, metoprolol, nadolol, oxprenolol, pindolol and propranolol;

(xxvi) cardiac inotropic agents selected from anrinone, digitoxin, digoxin, enoximone, lanatoside C and medigoxin;

(xxvii) corticosteroids selected from beclomethasone, betamethasone, budesonide, cortisone acetate, desoxymethasone, dexamethasone, fludrocortisone acetate, flunisolide, fluocortolone, fluticasone propionate, hydrocortisone, methylprednisolone, prednisolone, prednisone and triamcinolone;

(xxviii) diuretics selected from acetazolamide, amiloride, bendroflumethiazide, bumetanide, chlorothiazide, chlorthalidone, ethacrynic acid, frusemide, metolazone, spironolactone and triamterene;

(xxix) gastrointestinal agents selected from bisacodyl, cimetidine, cisapride, diphenoxylate HCl, domperidone, famotidine, lanosprazole, loperamide, mesalazine, nizatidine, omeprazole, ondansetron HCl, pantoprazole, rabeprazole sodium, ranitidine HCl and sulphasalazine;

(xxx) histamine $H_1$- and $H_2$-receptor antagonists selected from acrivastine, astemizole, chlorpheniramine, cinnarizine, cetrizine, clemastine fumarate, cyclizine, cyproheptadine HCl, dexchlorpheniramine, dimenhydrinate, fexofenadine, flunarizine HCl, loratadine, meclizine HCl, oxatomide, and terfenadine;

(xxxi) keratolytic agents selected from acetretin, calciprotriene, calcifediol, calcitriol, cholecalciferol, ergocalciferol, etretinate, retinoids, targretin, and tazarotene;

(xxxii) lipid regulating/hypolipidemic agents selected from atorvastatin, bezafibrate, cerivastatin, ciprofibrate, clofibrate, fenofibrate, fluvastatin, gemfibrozil, hesperetin, lovastatin, pravastatin, probucol, and simvastatin;

(xxxiv) muscle relaxants selected from cyclobenzaprine, dantrolene sodium and tizanidine HCl;

(xxxv) opioid analgesics selected from codeine, dextropropoxyphene, diamorphine, dihydrocodeine, fentanyl, meptazinol, methadone, morphine, nalbuphine and pentazocine;

(xxxvi) sex hormones selected from clomiphene citrate, cortisone acetate, danazol, dehydroepiandrosterone, ethynyl estradiol, finasteride, fludrocortisone, fluoxymesterone, medroxyprogesterone acetate, megestrol acetate, mestranol, methyltestosterone, mifepristone, norethisterone, norgestrel, oestradiol, conjugated estrogens, progesterone, rimexolone, stanozolol, stilbestrol, testosterone and tibolone;

(xxxvii) stimulants selected from amphetamine, dexamphetamine, dexfenfluramine, fenfluramine and mazindol;

(xxxviii) nutraceutical agents selected from calcitriol, carotenes, chrysin, dihydrotachysterol, flavonoids, hesperitin, jasmonates, lipoic acid, lutein, lycopene, essential fatty acids, non-essential fatty acids, naringenin, phytonadiol, quercetin, vitamins including vitamin A, vitamin B2, vitamin D and derivatives, vitamin E, and vitamin K, coenzyme Q10 (ubiquinone), plant extracts, and minerals.

Preferred lipophilic active compounds used in the present invention are the drugs fenofibrate, atorvastatin, clarithromycin, itraconazole, nifedipine, albendazole, and tacrolimus; the veterinary drugs albendazole, itraconazole and fenbendazole; and the nutraceuticals hesperetin and resveratrol.

As defined according to the invention, at least one of the two or more polymers entrapping the lipophilic active compound must be an amphiphilic polymer and at least one of the other two or more polymers may be an amphiphilic polymer of a different hydrophobic-hydrophilic balance or a hydrophilic polymer, thus creating a broad hydrophobic-hydrophilic range.

Examples of amphiphilic polymers suitable for use in the invention include, but are not limited to, polyethylene oxides (PEO) (also commonly referred to as polyethylene glycol or PEG), PEO derivatives, PEO copolymers such as PEO/polypropylene glycol (PPG) copolymers, PEG-modified starches, poloxamers, poloxamines, polyvinylpyrrolidones (PVP), hydroxypropyl cellulose, hypromellose and esters thereof, vinyl acetate/vinylpyrrolidone random copolymers, polyacrylates and copolymers thereof, polymethacrylates and copolymers thereof, polyacrylic acid copolymers, polymethacrylic acid copolymers, plant proteins and plant protein hydrolysates.

In one embodiment, the amphiphilic polymer is polyethylene glycol (PEG) or polyethylene oxide (PEO) or a derivative thereof. PEG/PEO refers to an oligomer or polymer of ethylene oxide with different molecular weights. Derivatives of PEG/PEO include ethers, preferably $C_1$-$C_{14}$ alkyl ethers, more preferably the methyl ether (mPEG).

In a preferred embodiment of the invention, the amphiphilic polymer is a block copolymer. In a more preferred embodiment, the block copolymer is a poloxamer. Poloxamers are block copolymers of PEG and PPG, composed of a central hydrophobic block of polypropylene glycol (PPG) flanked by two hydrophilic blocks of polyethylene glycol (PEG). The lengths of the polymer blocks can be customized and thus many different poloxamers exist that have slightly different properties such as poloxamer 188, 335 and 407. In one preferred embodiment of the invention, the amphiphilic polymer is Poloxamer 407, also known by the BASF trade name Lutrol F-127, which has approximately 101 repeat units of the two PEG blocks and approximately 56 repeat units of the propylene glycol block. Poloxamines are tetrafunctional block copolymers consisting of four PEG/PPG blocks centered on an ethylenediamine moiety.

In another embodiment, the amphiphilic polymer is a polyvinylpyrrolidone (PVP) or a copolymer thereof, particularly Copovidone, a 4-vinylpyrrolidone-vinyl acetate copolymer.

Hypromellose stands for hydroxypropyl methylcellulose (HPMC) and esters thereof include hypromellose phthalate (HPMCP) and hypromellose acetate succinate (HPMCAS).

The protein hydrolysates useful as amphiphilic polymers according to the invention can be a plant protein hydrolysate such as wheat, soy, rice, corn or flaxseed protein hydrolysate. Examples of proteins hydrolysates include wheat gluten hydrolysate; examples of proteins useful as amphiphilic polymers include corn zein.

In preferred embodiments of the invention, the amphiphilic polymer is a poloxamer, more preferably Poloxamer 407, polyvinylpyrrolidone (PVP), Copovidone, a protein, a protein hydrolysate, or a combination thereof.

Examples of hydrophilic polymers suitable for use in the invention include, but are not limited to, starch, sodium carboxymethylcellulose (NaCMC), hydroxyethylcellulose, polyvinyl alcohol, an alginate such as sodium alginate, chitosan, and carrageenan.

In preferred embodiments of the invention, the hydrophilic polymer is NaCMC, sodium alginate or chitosan.

According to the present invention, amphiphilic and hydrophilic polymers as described above with different molecular weights can be used. Preferred for use in the invention are pharmaceutically acceptable polymers, more preferably polymers approved for human use.

The composition according to the invention may comprise two or more polymers, more preferably two or three polymers.

In one preferred embodiment, the composition of the invention comprises two polymers, wherein one is amphiphilic and the other is a hydrophilic polymer. In preferred embodiments, the amphiphilic polymer is Poloxamer 407 or Copovidone and the hydrophilic polymer is NaCMC, sodium alginate or chitosan.

In another preferred embodiment, both polymers in the composition of the invention are amphiphilic polymers, for example, hypromellose and esters thereof, e.g. hypromellose acetate succinate, hypromellose phthalate, and protein hydrolysate, e.g., wheat gluten, or PVP and a plant protein, e.g., corn zein.

In a further preferred embodiment, the composition of the invention comprises three polymers. In one embodiment, one of the three polymers is an amphiphilic polymer and the other two are hydrophilic polymers. In another embodiment, the three polymers are amphiphilic polymers, each having a different hydrophobic-hydrophilic balance. In a further more preferred embodiment, two of the three polymers are amphiphilic polymers, each having a different hydrophobic-hydrophilic balance, for example Poloxamer 407 and PVP, or PVP and protein hydrolysate, e.g. wheat gluten, and the third polymer is a hydrophilic polymer, preferably NaCMC.

In a more preferred embodiment, the at least one active compound is at least one lipophilic drug and the composition of the invention is a pharmaceutical composition comprising at least one lipophilic drug wrapped within a polymeric matrix formed by two or more polymers, wherein said polymeric matrix is not crosslinked and no covalent interaction occurs between the two or more polymers and between the polymers and the at least one lipophilic drug.

The pharmaceutical composition of the invention may comprise at least one lipophilic drug selected from the group of lipophilic drugs recited above in the specification, preferably fenofibrate, atorvastatin, clarithromycin, itraconazole, nifedipine, albendazole, hesperetin or tacrolimus.

In one preferred embodiment, the pharmaceutical composition comprises a sole lipophilic drug.

In one more preferred embodiment, the sole lipophilic drug is fenofibrate, a drug used to treat high cholesterol and high triglyceride levels. In one embodiment, the pharmaceutical fenofibrate composition comprises fenofibrate and two polymers forming the polymeric matrix, wherein one of the polymers is an amphiphilic polymer, preferably Poloxamer 407 and the other polymer is a hydrophilic polymer, preferably NaCMC or sodium alginate.

In one embodiment, the invention provides a pharmaceutical composition comprising about 5%-50%, preferably about 15%-35%, by weight of fenofibrate, about 10%-60%, preferably about 25%-50%, by weight of Poloxamer 407 and about 10%-60%, preferably about 25%-50%, by weight of NaCMC or sodium alginate.

In another embodiment, the pharmaceutical fenofibrate composition of the invention comprises fenofibrate and three polymers forming the polymeric matrix, wherein one of the three polymers is an amphiphilic polymer and the other two polymers are hydrophilic polymers.

In a further embodiment, the pharmaceutical fenofibrate composition of the invention comprises fenofibrate and three polymers forming the polymeric matrix, wherein two of the three polymers are amphiphilic polymers with different hydrophobic-hydrophilic balance, for example, Poloxamer and PVP or PVP and a protein hydrolysate, e.g., wheat gluten, and the third polymer is a hydrophilic polymer, preferably NACMC.

In another embodiment, the pharmaceutical composition of the invention comprises atorvastatin as the sole lipophilic drug. In one embodiment, the pharmaceutical atorvastatin composition comprises two polymers forming the polymeric matrix, wherein one of the polymers is an amphiphilic polymer, preferably Poloxamer 407, and the second polymer is a hydrophilic polymer, preferably NaCMC or sodium alginate. This pharmaceutical composition preferably comprises about 5%-50% by weight of atorvastatin, about 10%-60% by weight of Poloxamer 407 and about 10%-60% by weight of NaCMC or sodium alginate.

In another embodiment, the pharmaceutical composition of the invention comprises itraconazole as the sole lipophilic drug. In one embodiment, the pharmaceutical itraconazole composition comprises two polymers forming the polymeric matrix, wherein one of the polymers is an amphiphilic polymer, preferably Poloxamer 407, and the other polymer is a hydrophilic polymer, preferably NaCMC, sodium alginate or chitosan.

In one embodiment, the invention provides a pharmaceutical composition comprising about 5%-50% by weight of itraconazole, about 10%-60%, preferably about 25%-50%, by weight of Poloxamer 407 and about 10%-60%, preferably about 25%-50%, by weight of NaCMC or sodium alginate.

In another embodiment, the pharmaceutical composition of the invention comprises itraconazole and two amphiphilic polymers forming the polymeric matrix, wherein the two amphiphilic polymers are polyvinylpyrrolidone and a plant protein such as corn zein.

In other preferred embodiments, the pharmaceutical composition according to the invention comprises tacrolimus, nifedipine, clarithromycin, or albendazole as the sole lipophilic drug and two polymers forming the polymeric matrix, wherein one of the polymers is an amphiphilic polymer, preferably Poloxamer 407, and the other polymer is a hydrophilic polymer, preferably NaCMC.

The pharmaceutical compositions of the present invention may comprise the lipophilic drug and additional drugs, preferably one additional drug.

In one embodiment, the additional drug is a lipophilic drug present from the beginning in the feed solution used for the preparation of the composition (see description of the method of preparation hereinafter) and both lipophilic drugs are interwoven with the polymer matrix as a result of self-assembling and each of them has modified physico-chemical properties as compared to the bulk lipophilic drug used as starting material for preparation of the composition. In one preferred embodiment, such a composition comprises both fenofibrate and atorvastatin wrapped within a polymer matrix of Poloxamer 407 and NaCMC.

In another embodiment, the composition of the invention comprises the lipophilic drug interwoven with the polymeric matrix and another drug that may be lipophilic or not and is not a part of the lipophilic drug-polymer complex according to the invention and thus has not modified physico-chemical properties. Such a composition is prepared by physically mixing or formulating a solid composition of the invention with the additional drug. For example, the composition may be in the form of capsules containing granules of the solid composition of the invention and granules containing the additional drug blended and filled to capsules or in the form of tablets such as bilayered tablets comprising a layer of the solid composition of the invention and a layer of the additional drug. In one preferred embodiment, such a composition comprises fenofibrate interwoven with a polymer matrix of Poloxamer 407 and NaCMC and aspirin formulated with lactose in the form of capsules or bilayered tablets.

The selection of the additional drug in the composition of the present invention comprising two drugs is made in accordance with the therapeutic need. For example, for treatment of cardiovascular diseases or disorders, suitable drugs for combined administration are lipid regulating agents, anticoagulants, antidiabetics and antihypertensive drugs such as alpha- and/or beta-blockers, calcium channel blockers, angiotensin receptor blockers, and angiotensin converting enzyme (ACE) inhibitors. In the field of cancer therapy, suitable drugs for combined administration include, but are not limited to, two anticancer agents having different mechanisms of action or an anticancer agent with a P-glycoprotein (P-gp) inhibitor known to limit rapid elimination and to increase the bioavailability of the anticancer agent.

In one embodiment, the pharmaceutical composition of the present invention comprises a combination of two or more drugs of the same pharmaceutical category, such as two or more lipid regulating agents. Specifically, suitable drugs for combined administration in this case are fenofibrate and statins or HMG CoA reductase inhibitors useful to control hypercholesterolemia. In one preferred embodiment, the pharmaceutical composition of the invention comprises a combination of fenofibrate and atorvastatin.

In a further embodiment, the lipophilic active compound is a veterinary drug and the invention provides a veterinary composition comprising at least one lipophilic veterinary drug interwoven with a polymeric matrix formed by two or more polymers, wherein said polymeric matrix is not crosslinked and no covalent interaction occurs between the two or more polymers and between the polymers and the at least one lipophilic veterinary drug. In one embodiment, the veterinary composition comprises itraconazole and a polymer matrix formed by an amphiphilic polymer, preferably Poloxamer 407, and a hydrophilic polymer, preferably chitosan or NaCMC, or the polymer matrix is formed by two amphiphilic polymers, preferably PVP and corn zein. In other embodiments, the veterinary composition comprises albendazole or fenbendazole and a polymer matrix formed by an amphiphilic polymer, preferably Poloxamer 407, and a hydrophilic polymer, preferably NaCMC, In still a further embodiment, the lipophilic active compound is a nutraceutical and the invention provides a nutraceutical composition comprising at least one lipophilic nutraceutical interwoven with a polymeric matrix formed by two or more polymers, wherein said polymeric matrix is not crosslinked and no covalent interaction occurs between the two or more polymers and between the polymers and the at least one lipophilic nutraceutical. In one preferred embodiment, the lipophilic nutraceutical is resveratrol and two polymers form the polymeric matrix, wherein one of the polymers is an amphiphilic polymer, preferably Poloxamer 407, and the other is a hydrophilic polymer, preferably NaCMC, sodium alginate or chitosan. In another embodiment, the nutraceutical is hesperetin.

The nutraceutical composition of the invention may comprise other nutraceuticals or nutrients and dietary supplements.

In another aspect, the invention provides a method for the preparation of a composition of the invention, the method comprising the steps of:

(i) preparing a clear to opalescent and homogeneous solution of the polymers and the at least one lipophilic drug in a mixture of water and organic solvent, to form a polymers-lipophilic drug complex; and (ii) drying the polymers-lipophilic drug complex clear solution of (i) to form the composition as a dry powder.

The polymers-lipophilic drug clear and homogeneous solution can be prepared in various ways according to the polymers used. The lipophilic drug is always dissolved in an organic solvent that is miscible with water and does not lead to precipitation of the polymers when the organic solution containing the lipophilic drug is added to the polymers aqueous solution. Examples of such solvents include, but are not limited to, acetic acid, acetonitrile, acetone, 1-butanol, 2-butanol, N,N-dimethylacetamide; N,N-dimethylformamide, dimethyl sulfoxide, 1,4-dioxane, ethanol, formic acid, methanol, 3-methyl-1-butanol, methylethyl ketone, 2-methyl-1-propanol, 1-methyl-2-pyrrolidone, 1-pentanol, n-propanol, 2-propanol and tetrahydrofuran. In preferred embodiments, the organic solvent is n-propanol, ethanol, 1-vinyl-2-pyrrolidone or acetonitrile.

In one embodiment of the invention, the polymers-lipophilic drug clear and homogeneous solution is prepared by adding a solution of the lipophilic drug in an organic solvent to a homogeneous water solution of the polymers. The final solution consists of at least 50% by weight of water and less than 50% by weight of the organic solvent. The hydrophilic polymer has to dissolve both in water and in the mixture of organic solvent and water. This aqueous composition is crucial for the lipophilic drug-polymer complex formation. It should be noted that such a procedure has not been described in the prior art and is unexpected and non-obvious when dealing with solubilization of lipophilic actives.

The method above is suitable, for example, when one of the polymers is amphiphilic such as Poloxamer 407, and the other is hydrophilic such as NaCMC. As shown in the Examples hereinafter, fenofibrate was dissolved in n-propanol and added to an aqueous solution of Poloxamer 407 and NaCMC (Example 4); atorvastatin was dissolved in 1-methyl-2-pyrrolidone and added to an aqueous solution of Poloxamer 407 and NaCMC (Example 19); atorvastatin and fenofibrate were dissolved in 1-methyl-2-pyrrolidone and added to an aqueous solution of Poloxamer 407 and NaCMC (Example 21); and itraconazole was dissolved in acetonitrile and added to an aqueous solution of Poloxamer 407 and NaCMC (Example 24).

In another embodiment, the method comprises adding the amphiphilic polymer and optionally water to the lipophilic drug organic solution, and then adding the lipophilic drug-amphiphilic polymer solution to an aqueous organic solvent solution of a hydrophilic polymer. The organic solvent used for dissolving the hydrophilic polymer may be the same used for dissolving the lipophilic drug or may be a different solvent. In a preferred embodiment, it is the same solvent. Thus, in this way, the polymers-atorvastatin composition of Example 20 was prepared by dissolving atorvastatin and Poloxamer 407 in n-propanol and adding this solution to a solution of sodium alginate in aqueous n-propanol; and the polymers-itraconazole composition of Example 23 was prepared by dissolving itraconazole and Poloxamer 407 in n-propanol and adding this solution to a solution of chitosan in aqueous n-propanol.

As described above, compositions of the invention comprising two lipophilic drugs A and B can be prepared by the method above or by a different method. In one embodiment, the two drugs A and B are interwoven in combination with the same polymeric entity by the above method, producing the dry powder containing the drugs A-B-polymers complex, and both drugs undergo thermal behavior modification as defined. In another embodiment, each of the two drugs is interwoven separately with the same or different polymeric entity by the above method, producing one dry powder containing the drug A-polymers complex and another dry powder containing the drug B-polymers complex, which are then mixed, and in which each of the drugs undergo thermal behavior modification as defined. In a third embodiment, drug A is interwoven with the polymeric entity by the above method and undergoes thermal behavior modification as defined, while drug B is not formulated and simply mixed with the dry powder containing the drug A-polymers complex and drug B does not undergo thermal behavior modification.

An important step in the method of the invention is the drying of the polymers-lipophilic active compound clear and homogeneous solution, thus obtaining a powder consisting of polymers-lipophilic active compound complex particles having a hydrophobic-hydrophilic gradient to ensure solubilization. Contrary to the drying process described in U.S. Pat. No. 6,696,084, the method of the present invention is carried out on a clear and homogeneous solution of the polymers-lipophilic drug complex and does not use phospholipid surface active substance(s) nor a bulking agent such as sucrose to stabilize the lipophilic drug against particle size growth and agglomeration.

Any conventional method known for drying solutions such as, but not limited to, spray drying, evaporation by heating under vacuum, and freeze drying can be used according to the invention. In one more preferred embodiment of the invention, the powder composition is prepared by the spray drying method.

Upon contact with water or a biological fluid inside the body the powder obtained after spray drying according to the invention is converted into a colloidal dispersion that contains particles with size in the nanoscale range. For example, about 70% of the particles may have a size less than 2000 nm, preferably less than 1500 nm, less than 1200 nm and more preferably less than 1000 nm.

In the method of the invention, when an amphiphilic and a hydrophilic polymer are used to form the composition with the drug, the weak interaction between the two polymers and between the two polymers and the drug occurs even in the initial organic solvent-water mixture. As this medium is not a good solvent for the hydrophilic polymer and for the hydrophobic drug, both of them can be stabilized via complexation with the amphiphilic polymer. In the same way, when two amphiphilic polymers of different hydrophobic-hydrophilic balances are used to form the composition, the weak interaction between the two polymers occurs in the organic solvent-water mixture. As this medium is not a good solvent for the amphiphilic polymer which is more hydrophilic, the latter can be stabilized via complexation with the amphiphilic polymer which is more hydrophobic The spray-drying process ensures a strengthening of the interactions between the polymers themselves and between the polymers and the lipophilic active compound, and this step is thus essential for the preparation of the polymers-lipophilic active compound complex of the invention. In the course of drying, a gradual enrichment of the solvent mixture with water occurs, thus the self-assembly polymers-lipophilic active compound complex is formed mostly in an aqueous environment.

Although we do not wish to be bound by any particular theory, it appears that the method of the invention provides for "fixation" and stabilization of the lipophilic active compound/drug within the polymeric entity in such a way that the active compound/drug interacts with the hydrophobic components of the amphiphilic polymer complex and the hydrophilic components orient themselves outward towards the aqueous media, ensuring the solubilization of the lipophilic active compound/drug.

Introduction of the dried powder into water or aqueous medium does not necessitate a reorganization of the polymers-drug complex system, as the complex disperses itself in the same manner as it was formed. In contact with water or with a biological fluid in the body, nanodispersions are obtained that comprise nanosized particles of the polymers-lipophilic drug complex. These factors facilitate rapid dissolution, immediate release and improved bioavailability of the lipophilic drug.

In the compositions of the present invention, the lipophilic drugs have modified physico-chemical properties as compared to the bulk crystalline starting product and appear not to be pure particles of the drug coated by polymers, but rather a complex between the drug and the two or more polymers formed via self-assembly. The distinction between the compositions of the present invention and those described in the prior art is furthered by a built-in hydrophobic-hydrophilic gradient, which maintains integrity and internal order upon dispersion in water and facilitates release into aqueous media. This combination of the properties results in optimal characteristics of immediate release and a high bioavailability of the lipophilic drug.

It is a finding of the present invention that for the formulation to exhibit superior characteristics as described above one of the polymers must be amphiphilic (A) and the other may be either amphiphilic (B) with different balance of hydrophobic and hydrophilic segments in the polymer chain than polymer (A), or hydrophilic (C).

The polymer weight ratio is selected so that the interaction between the two polymers produces a polymeric entity that interacts with the lipophilic drug at an optimal polymer to lipophilic drug weight ratio in such a way as to bring the lipophilic drug to the modified thermal behavior with decreased enthalpy of melting or decrease of both enthalpy and temperature of melting of the lipophilic drug. In this context, it should be considered that for a higher bioavailability of the lipophilic drug, it might not be sufficient to reduce its particles to a nanosize. Besides the nanosized particles, the degree of modification of the drug physico-chemical properties is important: the highest bioavailability is achieved by the highest modification. For example, for loading 25% of lipophilic drug, the ratio between the amphiphilic and the hydrophilic polymer (or the amphiphilic polymer with a higher hydrophilicity) should be 2:1. For a higher concentration of lipophilic drug, this ratio may not be suitable and a higher proportion of the amphiphilic polymer may be needed. If a lower concentration of lipophilic drug is loaded, a higher degree of melting enthalpy and melting temperature depression can be achieved when the proportion of the amphiphilic polymer in the polymeric entity is lower.

As defined herein, when a composition of the invention comprises two or three amphiphilic polymers, they should have different hydrophobic-hydrophilic balances. According to the invention, the polymers-lipophilic drug formulations have a hydrophobic-hydrophilic gradient running from the hydrophobic range (due to the lipophilic drug and the hydrophobic portion of the amphiphilic polymer of lower hydrophilicity) to the hydrophilic range (due to the hydrophilic polymer or the hydrophilic portion of the amphiphilic polymer having higher hydrophilicity).

The design of the polymeric entity is based on interactions between the amphiphilic polymer with the hydrophilic polymer or with an amphiphilic polymer of different hydrophobic-hydrophilic balance. Non-covalent bonds are formed between the polymers and said bonds include donor-acceptor and/or electrostatic interactions and hydrogen bonding. The ratio between the two polymers amphiphilic:hydrophilic can be from 0.1:0.9 to 0.9:0.1 (more amphiphilic polymer is preferred in order to get a larger degree of melting enthalpy depression), and the loading of the lipophilic drug into the polymer mixture is about 5-50%. In this context, formulations of the prior art using only one amphiphilic polymer or only one hydrophilic polymer, do not allow for creation of a hydrophobic-hydrophilic gradient which enables stable solid dispersion and other optimal characteristics (Examples 2, 3 and 10). The compositions of the invention consisting of the polymers-lipophilic drug complex powder obtained by the method of the invention are stable during at least twelve months, as shown in Example 13 hereinbelow. When the powder is dispersed in water or in an aqueous environment such as a biological fluid in the body, a colloidal dispersion with nanosized particles is obtained.

For prediction of the components—lipophilic active substance and polymers—interactions and creation of the hydrophilic-hydrophobic gradient of the polymers with the active compound, the solubility parameters for the components of the composition of the invention can be calculated. The solubility parameter is a tool that can be used for screening polymer-polymer and polymer-active compound interactions as described by Hildebrand et al. (Hildebrand, J H, Scott R L, The Solubility of Non-electrolytes. Reinhold, $3^{rd}$ edition, 1949, New York). In recent years, several research groups have applied solubility parameters in order to predict drug-polymer miscibility or compatibility and correlate this with performance-related characteristics of drug delivery systems (see, for example, Wu C, McGinty J W. 1999. Non-traditional plasticization of polymeric films. Int. J. Pharm 177:15-27; Sears J K, Touchette N W. 1982. Plasticizers. In: Mark H F, Othmer D F, Overberger C G, Seaborg G T, editors. Kirk-Othmer Encyclopedia of Chemical Technology, Vol. 18. New York: Wiley, pp 111-182).

The total and partial solubility parameters that are identified with cohesion energy density can be calculated and compared. It is generally accepted that for compatibility or miscibility of materials the difference between their solubility parameters has to be as small as possible. For many materials, the cohesive energy is defined not only by dispersion forces, but is dependent on the interaction between the polar groups of the material and on hydrogen bonding. Thus, the total solubility parameter ($\delta$) may be divided into three parts corresponding to three types of interactions: $\delta_d$-contribution of dispersion forces; $\delta_p$-contribution of polar forces, $\delta_h$-contribution of hydrogen bonding. All these contributions for the formulation components (drugs and polymers) can help to predict the extent of the drug and amphiphilic polymer miscibility, and also allow for the selection of proper components for induction of the hydrophobic-hydrophilic gradient. Thus, in this way, we can find the polymers which, according to their solubility parameters, may serve as a bridge between the lipophilic drug and the amphiphilic and/or hydrophilic polymers or segments and the aqueous media. These polymers allow the design of the integral lipophilic drug-polymers complex with a hydrophobic-hydrophilic gradient.

In accordance with the present invention, the total and partial solubility parameters for a group of lipophilic active compounds and a selection of amphiphilic and hydrophilic polymers all approved by the FDA for use for oral administration in humans were calculated using the Group Contribution Method (GCM) (Van Krevelen. 1976, Properties of Polymers. Elsevier, pp. 129-159) with Molecular Modeling Pro Plus software developed by Norgwyn Montgomery Software Inc. and are depicted in the table below. The solubility parameters values of the polymer that are closest to those of fenofibrate are demonstrated by the PPG block of Poloxamer (see the $\delta$ total). This is indicative that the interaction between fenofibrate and this polymer will be the most energetically favorable. Additional polymers having intermediate values, including the PEG block of Poloxamer and other amphiphilic polymers such as PVP, Copovidone, etc., serve as "bridges" to the hydrophilic polymers, which include NaCMC, chitosan, and PVA.

Table of solubility parameters for lipophilic drugs and polymers

| Solubility Parameters, $J^{1/2} \times cm^{-3/2}$ | | | $\Delta d$ | $\delta p$ | $\Delta h$ | $\delta t$ |
|---|---|---|---|---|---|---|
| Active Compounds | Fenofibrate | | 18.48 | 2.99 | 3.12 | 18.98 |
| | Atorvastatin | | 20.13 | 4.66 | 11.83 | 23.81 |
| | Itraconazole | | 23.6 | 8.45 | 7.43 | 26.15 |
| Polymers | PVP | | 22.72 | 22.84 | 9.89 | 24.94 |
| | Copovidone | | 23.44 | 4.03 | 10.14 | 25.86 |
| | Poloxamer | PPG | 19.17 | 0.76 | 11.08 | 22.16 |
| | Blocks | PEG | 20.85 | 13.99 | 13.2 | 24.71 |
| | PVA-PVAc | | 19.15 | 22.62 | 22.91 | 29.97 |
| | PVA | | 20.57 | 22.79 | 25.53 | 32.91 |
| | Chitosan | | 21.83 | 2.95 | 26.37 | 34.46 |
| | NaCMC | | 10.23 | 4.96 | 23.65 | 26.24 |

Other drugs such as itraconazole and atorvastatin, according to their solubility parameters, can be miscible with a number of different polymers, for example PVP, Copovidone, and Poloxamer. In these cases, hydrophilic polymers such as chitosan, NaCMC and PVA are most appropriate according to the table above.

Therefore, it can be seen that the solubility parameters used in this way aid the design of formulations with appropriate hydrophobic-hydrophilic gradients. In addition, it can be seen also that the use of two or more polymers according to the invention enables additional options for selecting suitable hydrophobic-hydrophilic ranges as well as allow a more customized design for active compound solubilization.

It should be understood that the term polymeric entity or polymer matrix as used herein does not relate to a pre-prepared polymer construct, but rather to an entity or matrix of the polymers that self-assembles with the lipophilic drug. When a lipophilic active compound is introduced into a mixture of polymers according to the invention, it coordinates with the hydrophobic moieties of the amphiphilic polymer, which is also interacted with the hydrophilic polymer, forming a lipophilic drug-polymers complex thus fixating the lipophilic drug within the polymeric entity. The polymers-lipophilic drug complex is formed by self-assembly. This is contrary to lipophilic drug particulates known in the art prepared by milling or similar procedures.

As mentioned before, the interaction between a lipophilic active compound and hydrophobic moieties of the amphiphilic polymer result in modification of its physicochemical properties. Thus, the compositions of the present invention exhibit significant changes in thermal behaviour of the lipophilic active compound as compared to the bulk crystalline compound used as starting material for preparation of the composition. They demonstrate a notable decrease of enthalpy of melting or decrease of both enthalpy of melting and temperature of melting of the lipophilic active compound.

Although we do not want to be bound by any specific classification of the structure of the compositions of the invention, these compositions may include eutectic mixtures, solid solutions or solid suspension with crystalline, partial and complete amorphous dispersed lipophilic drug phase.

Besides resulting in a modification of the lipophilic active compound thermal behavior, interaction between the two or more polymers and the lipophilic active compound creates a hydrophobic-hydrophilic gradient, which enables formation of a colloidal nanodispersion upon contact of the said composition with aqueous media that in turn facilitates immediate release and high bioavailability of the lipophilic active compound.

In another aspect, the present invention relates to a clear and homogeneous solution comprising two or more polymers and a lipophilic active compound in an aqueous solvent consisting of at least 50% by weight water and less than 50% by weight organic solvent in single phase, that does not undergo sedimentation or precipitation, wherein at least one of the two or more polymers is an amphiphilic polymer and at least another of the two or more polymers is either a hydrophilic polymer or an amphiphilic polymer with a hydrophobic-hydrophilic balance different from the first amphiphilic polymer.

In preferred embodiments, the lipophilic active substance is a lipophilic drug, such as, but not limited to, fenofibrate, atorvastatin, itraconazole, clarithromycin, nifedipine, albendazole, hesperitin and tacrolimus, the amphiphilic polymer is as defined hereinbefore, preferably Poloxamer 407, PVP, copovidone, a plant protein or a protein hydrolisate, and the hydrophilic polymer is as defined hereinbefore, preferably, NaCMC, sodium alginate and chitosan.

The pharmaceutical composition according to the present invention comprises the powder consisting of the lipophilic drug-polymers complex of the invention and may further comprise one or more pharmaceutically acceptable inert carriers or excipients or both such as binders, diluents, disintegrants, fillers, glidants, lubricants, suspending agents, sweeteners, flavoring agents, buffers, wicking agents, wetting agents, and effervescent agents.

When a binding agent is present in the composition, preferred binding agents include polyvinylpyrrolidone, starch, cellulose, e.g. crystalline cellulose, sucrose, D-mannitol, dextrin, hydroxypropyl cellulose, hydroxypropylmethyl cellulose, starch, saccharose, gelatin, methyl cellulose, and the like When a diluent is present in the composition, preferred diluents include microcrystalline cellulose, lactose, dibasic calcium phosphate, mannitol, starch, sorbitol, sucrose, glucose, starch or mixtures thereof.

Disintegrants for use in the invention include crosslinked insoluble polyvinyl pyrrolidone (crosspovidone such as Kollidon CL, Kollidon CL-SF), starch and modified starches, croscarmellose sodium (crosslinked sodium carboxymethylcellulose), sodium starch glycolate (e.g. Explotab), alginic acid, alginates, calcium silicate, and mixtures thereof.

Examples of filling agents are microcrystalline cellulose, lactose, mannitol, and starch. Suitable lubricants, including agents that act on the flowability of the powder to be compressed, are colloidal silicon dioxide, talc, stearic acid, magnesium stearate, calcium stearate, and silica gel.

Glidants can be used to improve the flow characteristics of granulations and powders by reducing inter-particulate friction and are typically added to pharmaceutical compositions immediately prior to tablet compression to facilitate the flow of granular material into the die cavities of tablet presses. When used for tablet compression, suitable glidants include: calcium silicate, colloidal silicon dioxide, asbestos free talc, sodium aluminosilicate, powdered cellulose, microcrystalline cellulose, corn starch, sodium benzoate, calcium carbonate, magnesium carbonate, metallic stearates, magnesium lauryl sulfate, and magnesium oxide.

When a lubricant is present in the composition, a preferred lubricant is magnesium stearate. Sweeteners, if present, may be any natural or artificial sweetener.

Examples of useful suspending agents include, but are not limited to, surfactants such as stearyltriethanolamine, sodium laurylsulfate (SLS), laurylaminopropionic acid, lecithin, benzalkonium chloride, benzethonium chloride, glycerine monostearate and the like.

A wicking agent, defined as having the ability to draw water into the porous network of a delivery material, may be included in the core of a tablet formulation of the invention. The wicking agent can be a swelling or non-swelling wicking agent such as, for example, sodium lauryl sulfate, colloidal silicon dioxide, calcium silicate and low molecular weight PVP.

The pharmaceutical composition of the invention comprising the polymers-lipophilic drug complex and optionally one or more pharmaceutically acceptable inert carriers and/or excipients as described above may be employed as such. However, it is preferable to present the composition in the form of solid dosage forms such as capsules, tablets, beads, grains, pills, granulates, granules, powder, pellets, sachets, lozenges, troches, oral suspensions and aerosol. Preferred solid dosage forms include capsules, tablets, pills, granulates, granules, powder, oral suspensions and aerosol.

In one preferred embodiment, the pharmaceutical composition of the invention is formulated into a tablet.

The compositions of the invention show fast dissolution in tests performed in accordance with FDA Dissolution Methods for Drug Products. For lipophilic drugs with good permeability, wherein solubility is the main deterrent to achieve good bioavailability, dissolution tests are indicative of solubility and therein bioavailability.

Administration of the composition of the invention is expected to result in immediate release and improved bioavailability of the lipophilic drug.

The term "bioavailability" refers to the degree to which the lipophilic drug becomes available to the target tissue after administration. A suitable bioavailability for the lipophilic drug composition of the invention should show that administration of such a composition results in a bioavailability that is improved or is at least the same when compared to the bioavailability obtained after administration of the lipophilic drug raw crystalline powder or of a commercially available product containing the lipophilic drug in the same amounts.

It is also desirable that the lipophilic drug compositions of the invention show bioequivalency to, and/or improved pharmacokinetic (PK) profiles in comparison to, commercially available lipophilic drug compositions, namely, that they demonstrate similar or better pharmacokinetic profiles when given in similar doses under similar conditions. Parameters often used in bioequivalence studies are $t_{max}$, $C_{max}$, $AUC_{0-infinity}$, $AUC_{0-t}$. At least $C_{max}$ and AUC parameters may be applied when determining whether bioequivalence is present. The $t_{max}$ denotes the time to reach the maximal plasma concentration ($c_{max}$) after administration; $AUC_{0-infinity}$ or AUC denotes the area under the plasma concentration versus time curve from time 0 to infinity; $AUC_{0-t}$ denotes the area under the plasma concentration versus time curve from time 0 to time t, especially, $AUC_{0-24}$ is the area under the plasma concentration versus time curve from time 0 to time 24 hr at steady state conditions.

As shown herein in the examples, Table 4 depicts PK plot values (AUC, $C_{max}$) in rats for a group of fenofibrate formulations of Example 4 (formulations 4.1, 4.2, 4.11, 4.12). As can be seen, formulations 4.1 and 4.2 show significantly heightened values of AUC and $C_{max}$ when compared to the commercial micronized fenofibrate In contrast, formulations 4.11 and 4.12 were marginally better than micronized fenofibrate according to the same parameters. Therefore, these preclinical tests enabled us to screen out the less attractive formulations and focus on the two leading formulations for clinical studies as detailed in Example 15.

Table 8 gives a summary of the results for a pilot clinical study for formulations 4.1 and 4.2 as suspensions vs. a Tricor® 145 tablet. Formulation 4.2 showed $C_{max}$ values higher than those for the formulation 4.1. According the main PK parameters ($C_{max}$ and AUC) formulation 4.2 is very similar to the commercial Tricor® 145 tablet. This pilot study therefore indicates that formulation 4.2 could be the first choice for clinical studies.

The compositions of the invention comprising the polymers-lipophilic drug complex are useful for treating a disease, disorder or condition responsive to said lipophilic drug.

In one preferred embodiment, the lipophilic drug is fenofibrate and the compositions of the invention comprising the polymers-fenofibrate complex are useful for treating a disease, disorder or condition responsive to fenofibrate. They are thus useful for treating hyperlipidemia, a condition characterized by an elevation of lipids (fats) such as cholesterol, cholesterol esters, and triglycerides, in the bloodstream. Hyperlipidemia is associated with an increased risk of coronary heart disease (that can lead to angina pectoris, a heart attack, or both) and to thickening or hardening of the arteries that supply blood to the heart muscle. In particular, the compositions can be useful for treating conditions such as hypercholesterolemia, hypertriglyceridemia, cardiovascular disorders, coronary heart disease, and peripheral vascular disease (including symptomatic carotid artery disease).

Thus, in one embodiment, the present invention provides a method for treating hyperlipidemia, which comprises administering to an individual in need a therapeutically effective amount of a pharmaceutical composition of the invention comprising fenofibrate. In preferred embodiments, the method of the invention is useful for treatment of conditions such as hypercholesterolemia, hypertriglyceridemia, cardiovascular disorders, coronary heart disease, and peripheral vascular disease (including symptomatic carotid artery disease).

In another embodiment, the lipophilic drug is atorvastatin, an inhibitor of 3-hydroxy-3-methylglutaryl-coenzyme A (HMG-CoA) reductase, useful to reduce the amount of cholesterol and other fatty substances in the blood. Atorvastatin calcium is available as 10, 20, 40 and 80 mg tablets under the trademark Lipitor™ (Pfizer Inc.). In one preferred embodiment, the composition of the invention comprises a polymers-atorvastatin complex, in which the atorvastatin is interwoven with a Poloxamer 407-NaCMC polymeric entity. In another embodiment, the composition of the invention comprises a polymers-atorvastatin complex, in which the atorvastatin is interwoven with a Poloxamer 407-sodium alginate polymeric entity.

The atorvastatin compositions are useful for treating hyperlipidemia, a condition characterized by an elevation of lipids (fats) such as cholesterol, cholesterol esters, and triglycerides, in the bloodstream. Hyperlipidemia is associated with an increased risk of coronary heart disease (that can lead to angina pectoris, a heart attack, or both) and to thickening or hardening of the arteries that supply blood to the heart muscle.

In another embodiment, the present invention provides a pharmaceutical composition comprising a combination of two cholesterol regulating drugs-atorvastatin and fenofibrate in a polymers-fenofibrate/atorvastatin complex in which the fenofibrate and the atorvastatin are interwoven with a polymeric entity formed by Poloxamer 407 and NaCMC.

Thus, the present invention provides a method for treating hyperlipidemia, which comprises administering to an individual in need a therapeutically effective amount of a pharmaceutical composition of the invention comprising a polymers-atorvastatin complex or polymers-atorvastatin/fenofibrate complex.

In another embodiment, the lipophilic drug is itraconazole, an azole medicine used to treat fungal infections. It is effective against a broad spectrum of fungi including dermatophytes (tinea infections), yeasts such as candida and malassezia infections, and systemic fungal infections such as histoplasma, aspergillus, coccidiodomycosis, chromoblastomycosis. Itraconazole is available as 100 mg capsules under the trademark Sporanox™ (Janssen-Cilag). In one preferred embodiment, the composition of the invention comprises a polymers-itraconazole complex, in which the itraconazole is interwoven with a Poloxamer 407-sodium carboxymethylcellulose polymeric entity. In another preferred embodiment, the composition of the invention comprises a polymers-itraconazole complex, in which the itraconazole is interwoven with a Poloxamer 407-chitosan HCl polymeric entity. In a further preferred embodiment, the composition of the invention comprises a polymers-itraconazole complex, in which the itraconazole is interwoven with a polyvinylpyrrolidinone-protein, preferably corn zein, polymeric entity.

In one another embodiment, the lipophilic drug is tacrolimus, a macrolide immunosuppressant administered after allogenic organ transplant to reduce the activity of the patient's immune system and so the risk of organ rejection. Tacrolimus is available as 0.5, 1.0 and 5.0 mg capsules under the trademark Prograf™. In one preferred embodiment, the composition of the invention comprises a polymers-tacrolimus complex, in which the tacrolimus is interwoven with a Poloxamer 407-NaCMC polymeric entity.

The following examples illustrate certain features of the present invention but are not intended to limit the scope of the present invention.

EXAMPLES

In the examples below, where the term "ratio" is used, it refers to weight/weight ratio, except the cases where use of the other units is especially referred in the text.

Materials and Methods:

Materials: Fenofibrate (from ChemAgis, Israel); fenofibrate capsules containing micronized fenofibrate (200 mg) for oral administration with food (from Teva Pharmaceuticals Ltd., Israel); Tricor 145 tablets (from Abbott Laboratories); Atorvastatin calcium, Nifedipine and Clarithromycin (from Teva Pharmaceutical Industries Ltd., Israel); Itraconazole (BP micronized, from Hawkins Inc., USA); Sporanox (granules, from Janssen-Cilag); Tacrolimus (from Fermentek Ltd., Israel); Resveratrol (from Sigma); hesperitin, albendazole and fenbendazole (from Sito (China) International); Albazen (Rubikon, Byelorussia) [Poloxamer 407 (Lutrol F 127; BASF, Germany); chitosan HCl (from Kraeber GmbH); vinylpyrrolidone-vinylacetate copolymer (Copovidone K28, Kollidon VA64) and polyvinylpyrrolidone (PVP, Kollidon 30) (from BASF, Germany); carboxymethylcellulose sodium NaCMC (Aqualon CMC-7L2P, from Aqualon, Hercules Inc.); corn zein (from Sigma); sodium alginate (Protanal SF, from Protan Inc., USA); and polyvinylpyrrolidone (PVP K10, MW 10.000, from Sigma); protein hydrolysate from wheat gluten (HyPep 4601 from Sigma); sodium lauryl sulfate, sodium taurocholate, lecithin and aspirin (from Sigma-Aldrich); docusate sodium and sodium benzoate (from Cytec, USA); sodium starch glycolate (Explotab, from JRS Pharma, Germany); lactose (from Alfa Chem. USA); dextrates (from Penwest Pharmaceuticals Co., USA), Hypromellose Acetate Succinate (Shin-Etsu AQOAT, from Shin-Etsu, Japan), calcium silicate (from Sigma); 1-methyl-2-pyrrolidone (from Riedel-de-Haen); n-propanol (from Sigma).

Methods:

(i) Preparation of the solutions of polymers and active compounds—The liquid intermediates containing the active compound(s) and the polymers were prepared using Ekato Unimix LM3 mixer (Ekato Systems GmbH) and peristaltic pump and tubing.

(ii) The spray-drying process was conducted using Mini Spray Dryer B-290 of Buchi Labortechnik AG.

(iii) Tablet compression was performed with a Single Punch Tablet Press DP12-Shanghai Tianxiang & Chentai Pharmaceutical Machinery Co. Ltd.

(iv) The dissolution test was performed in accordance with USP Dissolution Method <711> and FDA Dissolution Methods for Drug Products using the paddle apparatus Distek model 2100A. The quantification was performed using UV spectrophotometer. Appropriate amount of spray dried powders or tablets as well as control powders or tablets were dissolved in 1000 ml of 0.05 M water solution of sodium lauryl sulfate, at 37° C., with rotation speed of 75 rpm and sampling time of 5, 10, 20 and 30 min for powders or 20, 30, 40 min for tablets.

(v) The tablets disintegration test was performed in accordance with USP Disintegration Method <701>

(vi) Thermal properties of the compositions were studied using standard DSC equipment such as Differential Scanning Calorimeter from Mettler Toledo, model DSC 820, Aluminum Crucibles standard 401 ME-27331, Mettler Toledo Balance MT-15, Sealer Press, Crucible handling set ME-119091, and Mettler-Toledo STAR$^e$ Software System. The samples (5-10 mg) were heated at a heating rate of 10° C./min from 25° C. to 100° C.

(vii) Particle size of the nanodispersions: measurements were performed using Dynamic Light Scattering (DLS). The method was run on the Malvern Zen 3600, Zetasizer-nano series. The samples were prepared by suspending spray-dried powder in water (0.075-0.1%) at 25-30° C. First, water was added to the appropriate amount of the powder and the mixture was left for 15 min. Then, the suspension was magnetically stirred during 4 min at 300 rpm and 1 ml of the suspension was transferred to a cuvette for measurement. The cuvette was incubated inside the instrument during 5 min for stabilization prior measurement. A series of at least 5 repeating measurements was carried out at 25-30° C. Following parameters are reported from the analysis of volume weighed size distribution: polydispersity index (PDI), the diameter of the main fraction (Z-vol), volume % of main fraction.

(viii) Concentrations of fenofibric acid in rat plasma were determined by HPLC-UV method using ThermoFinnigan Surveyor Instrument with ChromQuest 4.1 software.

(ix) Concentrations of fenofibric acid and resveratrol metabolites in human plasma as well as albendazole sulfoxide concentration in pig plasma were determined by validated HPLC-UV methods using Summit DI 6009 Dionex (Germany) HPLC system with photodiode array (PDA) detector and Chromeleon Version 6.70 software package.

Example 1

Spray-Dried Fenofibrate

Fenofibrate (1.0 g) was dissolved under stirring at 300 rpm in 17.6 gl of n-propanol at 45° C. Water (18 g) water was added to the fenofibrate solution at a feeding rate of 1 ml/min, under stirring at 300 rpm and at temperature 45° C. The resultant clear homogeneous solution was placed to the bath at 55° C. and spray dried using Buchi Mini Spray Drier with inlet air temperature 78° C. and outlet temperature 50° C., thus obtaining a powder. This powder was used in comparison studies hereafter.

Example 2

Formulation of Fenofibrate with NaCMC

Drug Solution:
Fenofibrate (1.0 g) was dissolved under stirring at 300 rpm in 89 g of n-propanol at 25° C.
Polymer Solution:
NaCMC (3.0 g) was dissolved under stirring at 300 rpm in water (100 g) at 43° C.
The drug solution was added to the polymer solution at a feeding rate of 2 ml/min, under stirring at 300 rpm and at temperature 45° C., then temperature was elevated to 56° C. The resultant clear homogeneous solution was spray dried from hot (50-55° C.) solution, using Buchi Mini Spray Drier with inlet air temperature 98° C. and outlet temperature 64° C., thus obtaining a powder. This powder was used in comparison studies hereafter.

Example 3

Formulation of Fenofibrate with Poloxamer 407

Drug Solution:
Fenofibrate (0.5 g) was dissolved under stirring at 300 rpm in 60 g of n-propanol at ambient conditions.
Polymer Solution:
Poloxamer 407 (1.5 g) was dissolved under stirring at 300 rpm in 75 g of water at ambient conditions.
The drug solution was added to the polymer solution at a feeding rate of 2 ml/min, under stirring at 300 rpm at temperature 25° C. The resultant clear homogeneous solution was spray dried using Buchi Mini Spray Drier with inlet air temperature 100° C. and outlet temperature 64° C., thus obtaining a viscous liquid, which forms a film on the cyclone after cooling. This film was removed and crushed using mortar and pestle. This powder was used in comparison studies hereafter.

Example 4

Fenofibrate Formulations Containing Poloxamer 407 and NaCMC

General procedure for preparation of formulations 4.1-4.14 in Table 1:
This example presents the matrix design for fenofibrate formulations comprising different ratios of fenofibrate (FFB), Poloxamer 407 (Lutrol F 127) and NaCMC. Loading of fenofibrate in the final dry powder is in the range of 25-33.3%, and the range of Lutrol F 127 and NaCMC is 22-50% for each. The dry formulations can contain also 2-8% of water. The content of all solids (FFB, Lutrol and NaCMC) in the liquid intermediate is also variable from 2.0% to 6.2% (w/w).
Drug Solution:
Raw crystalline fenofibrate (FFB) was dissolved under stirring at 300 rpm in n-propanol at 25° C.
Polymers Solution:
NaCMC and Poloxamer 407 were dissolved under stirring at 300 rpm in water at 45° C.
The drug solution was added to the polymers solution at a feeding rate in the range of 2-10 ml/min, under stirring at 300 rpm. The resultant clear homogeneous solutions were spray dried, yielding free-flowing powders. The mixing and drying parameters are summarized in Table 1.

TABLE 1

Mixing and drying parameters of fenofibrate, Lutrol and NaCMC

| Formulation No. | Mixing parameters | | | | | | Drying Parameters | |
|---|---|---|---|---|---|---|---|---|
| | FFB (g) | Lutrol (g) | NaCMC (g) | N-propanol (g) | Water (g) | Addition Temp (° C.) | Inlet Temp (° C.) | Outlet temp (° C.) |
| 1 | 15 | 15 | 30 | 1200 | 1500 | 40 | 120 | 72 |
| 2 | 15 | 30 | 15 | 1200 | 1500 | 40 | 110 | 64 |
| 3 | 45 | 90 | 45 | 1080 | 1650 | 55 | 110 | 64 |

TABLE 1-continued

Mixing and drying parameters of fenofibrate, Lutrol and NaCMC

| Formulation No. | Mixing parameters | | | | | | Drying Parameters | |
|---|---|---|---|---|---|---|---|---|
| | FFB (g) | Lutrol (g) | NaCMC (g) | N-propanol (g) | Water (g) | Addition Temp (° C.) | Inlet Temp (° C.) | Outlet temp (° C.). |
| 4 | 2 | 3 | 3 | 160 | 200 | 30 | 80 | 55 |
| 5 | 0.56 | 0.48 | 0.96 | 40 | 50 | 30 | 100 | 63 |
| 6 | 0.56 | 0.72 | 0.72 | 40 | 50 | 30 | 80 | 55 |
| 7 | 0.56 | 0.96 | 0.48 | 40 | 50 | 30 | 80 | 52 |
| 8 | 0.60 | 0.93 | 0.47 | 40 | 50 | 30 | 80 | 54 |
| 9 | 0.60 | 0.70 | 0.70 | 40 | 50 | 30 | 80 | 55 |
| 10 | 0.60 | 0.47 | 0.93 | 40 | 50 | 30 | 100 | 63 |
| 11 | 0.67 | 0.89 | 0.44 | 40 | 50 | 30 | 80 | 52 |
| 12 | 0.67 | 0.44 | 0.89 | 40 | 50 | 30 | 100 | 62 |
| 13 | 2.67 | 2.67 | 2.67 | 160 | 200 | 30 | 100 | 75 |
| 14 | 0.18 | 0.57 | 0.25 | 50 | 50 | 48 | 96 | 64 |

The formulations 1-14 above are referred to in the description and in the following examples as Examples/formulations 4.1 to 4.14, respectively.

Example 5

Fenofibrate Formulation Containing Poloxamer 407 and Sodium Alginate

Solution a Containing Fenofibrate and Poloxamer 407:
Fenofibrate (0.18 g) was dissolved in 16 g n-propanol at ambient conditions under stirring at 300 rpm. Then 5 g of water and 0.20 g of Poloxamer 407 were added under stirring.
Solution B Containing Sodium Alginate:
Sodium alginate (0.30 g; Protanal SF) was mixed with 4 ml of 1-propanol at ambient conditions under stirring at 300 rpm. Then 35 g of water was added under stirring and the mixture was heated up to 65° C. until full dissolution of polymer.
Solution A was added to solution B at a feeding rate of 2 ml/min, under stirring conditions (500 rpm) and at temperature 65° C. The resultant clear homogeneous solution was spray dried using Buchi Mini Spray Drier with inlet air temperature 100° C. and outlet temperature 70° C., thus obtaining a powder.

Example 6

Fenofibrate Formulation Containing Poloxamer 407, PVP and NaCMC

Drug Solution:
Fenofibrate (0.5 g) was dissolved in 32 g n-propanol at ambient conditions under stirring conditions (300 rpm).
Polymers Solution:
(a) NaCMC (0.5 g) was dissolved in 60 g water under stirring (300 rpm) at 50° C.; (b) Poloxamer 407 (0.5 g) was dissolved in solution (a) at 50° C.; (c) PVP 10 kDa (0.5 g) was dissolved in solution (b) at 50° C.; (d) 16 g n-propanol was added to solution (c), and then the polymers solution was heated up to 62-63° C., under stirring.
The drug solution was added to the hot polymers solution at a feed rate of 2 ml/min, under stirring at 300 rpm. The resulting transparent, homogeneous solution was spray dried using Buchi Mini Spray Drier with inlet air temperature 100° C. and outlet temperature 60° C., producing a powder.

Example 7

Fenofibrate Formulation Containing PVP, Protein Hydrolysate and NaCMC

Drug Solution:
Fenofibrate (0.7 g) was dissolved in 32 g n-propanol at ambient conditions under stirring conditions (300 rpm).
Polymers Solution:
(a) NaCMC (0.7 g) was dissolved in 60 g water under stirring at 47° C.; (b) 0.3 g protein hydrolysate (wheat gluten) was dissolved in solution (a) at ambient temperature; (c) PVP 10 kDa (0.3 g) was dissolved in solution (b) at ambient temperature; (d) 16 g n-propanol was added to solution (c), and then the polymer solution was heated up to 67-68° C., under stirring.
The drug solution was added to the hot polymers solution at a feed rate of 2 ml/min, under stirring at 300 rpm. The resulting transparent, homogeneous solution was spray dried using Buchi Mini Spray Drier with inlet air temperature 78° C. and outlet temperature 50° C., producing a powder.

Example 8

Fenofibrate Formulation Containing Copovidone K28 and NaCMC

Drug Solution:
Fenofibrate (1.25 g) was dissolved in 40 gl n-propanol at ambient conditions under stirring conditions (300 rpm).
Polymers Solution:
(a) NaCMC (1.25 g) was dissolved in 50 g water under stirring (300 rpm) at 40-45° C.; and (b) Copovidone K28 (2.50 g) was dissolved in solution (a) at 50° C.
The drug solution was added to the warm polymers solution (40-45° C.) at a feed rate of 2 ml/min, under stirring at 300 rpm. The resulting transparent, homogeneous solution was placed to the bath at 55° C. and spray dried using Buchi Mini Spray Drier with inlet air temperature 98° C. and outlet temperature 64-67° C., producing a powder.

Example 9

Fenofibrate Formulation Containing Hypromellose Acetate Succinate and Protein Hydrolysate Drug Solution:
Fenofibrate (0.5 g) was dissolved in 20 g n-propanol at ambient conditions under stirring conditions (300 rpm).
Polymers Solution:
(a) Hypromellose acetate succinate (1.0 g) was dissolved in 27 gl of n-propanol-water (45:55) mixture under stirring at 50° C.; and (b) Protein hydrolysate (1.0 g wheat gluten) was dissolved in 20 g of water at 56° C.

Drug solution was added to hot (60° C.) solution (a) under magnetic stirring (300 rpm) at a feed rate of 2 ml/min producing solution (c). The hot solution (c) was added to hot (60° C.) solution (b) at a feed rate of 2 ml/min under stirring at 300 rpm. The resulting transparent homogeneous solution was spray dried using Buchi Mini Spray Drier with inlet air temperature 80° C. and outlet temperature 55° C., producing a powder.

Example 10

Particle Size of Aqueous Dispersions Obtained from the Fenofibrate Formulations The powders produced as described in Examples 1-9 have been suspended in deionized water as described in method (vii) of the section Materials and Methods.

The powders of Examples 1-3 comprising fenofibrate alone or in combination with one sole polymer formed coarse suspensions with large visible particles. This kind of suspension is unsuitable for Dynamic Light Scattering measurement.

The powders of Examples 4-10 comprising fenofibrate-polymers formulations according to invention were converted to colloidal dispersion with particles size in the nanoscale range. The results are shown in Table 2.

TABLE 2

Characteristics of the fenofibrate colloidal dispersions

| Formulation | Number of measurements | z-vol of the main fraction, nm | PDI | % vol of the main fraction |
|---|---|---|---|---|
| Example 4.1 | 5 | 628 | 0.617 | 90 |
| Example 4.2 | 10 | 669 | 0.452 | 99 |
| Example 4.3 | 5 | 916 | 0.394 | 100 |
| Example 4.4 | 10 | 316 | 0.514 | 98 |
| Example 4.5 | 10 | 405 | 0.683 | 84 |
| Example 4.6 | 15 | 668 | 0.580 | 87 |
| Example 4.7 | 10 | 668 | 0.617 | 95 |
| Example 4.8 | 10 | 512 | 0.480 | 92 |
| Example 4.9 | 10 | 478 | 0.573 | 91 |
| Example 4.10 | 10 | 561 | 0.563 | 100 |
| Example 4.11 | 10 | 500 | 0.559 | 100 |
| Example 4.12 | 10 | 481 | 0.508 | 100 |
| Example 4.13 | 10 | 585 | 0.417 | 100 |
| Example 4.14 | 10 | 605 | 0.540 | 100 |
| Example 5 | 15 | 128 | 0.384 | 100 |
| Example 6 | 5 | 644 | 0.378 | 90 |
| Example 7 | 5 | 527 | 0.591 | 100 |
| Example 8 | 5 | 655 | 0.402 | 89 |
| Example 9 | 5 | 578 | 0.328 | 100 | z-vol is the mean diameter (in nm) of each definite fraction
PDI—polydispersity index The analysis of dispersions described in the present example show that only compositions of the invention possessing the hydrophobic-hydrophilic gradient are able to produce homogeneous nanodispersions. This inherent property ensures improvement in the bioavailability of fenofibrate.

In the Dynamic Light Scattering method, we used two main parameters to characterize the colloidal system: the hydrodynamic diameter of the particles and the width of distribution (polydispersity). Unimodal dispersions are well characterized by Gaussian distribution with mean particle diameter (z-average) In the case of multimodal system, a much more complex analysis is required. The algorithms used provide information about mean diameter, and width and peak mode for each fraction. The most realistic view of a material distribution to fractions can be obtained from volume weighted particle size distribution analysis (Shekunov et al., Particle size analysis in pharmaceutics. Pharmaceutical Research, 2007, vol. 24(2), p. 203). The term z-vol is used in this analysis to characterize the mean diameter of each definite fraction. PDI is used to characterize the reliability of particles size distribution analysis. The values between 0.08 and 0.7 belong to a mid-range polydispersity. It is the range trough which the DLS distribution algorithm operates in the best way. The values above 0.7 mean that the sample is too polydisperse and not suitable for DLS technique.

As shown in Table 2, all dispersions of Examples 4-9 demonstrate mid-range polydispersity (PDI in the range from 0.08 to 0.7). The high percentages of main fraction indicate a substantially unimodal (homogeneous) distribution of the nanocolloidal particles dispersion.]

Example 11

Thermal Properties of Fenofibrate Formulations

In order to determine the thermal properties of fenofibrate in the compositions of the invention, the temperature ($T_{melt}$) and the enthalpy ($\Delta H_{melt}$) of melting of spray-dried powders obtained in the previous examples were determined by Differential Scanning Calorimetry (DSC) as described in Methods section. These characteristics were compared to thermograms of starting commercial raw fenofibrate as well as of commercial fenofibrate drug products. The enthalpy of fenofibrate melting is given in Joule per gram of fenofibrate ($J/g_{FF}$). The results are shown in Table 3.

TABLE 3

DSC of fenofibrate formulations

| Sample | $T_{melt}$ (° C.) | $\Delta H_{melt}$ ($J/g_{FF}$) |
|---|---|---|
| Fenofibrate starting material | 81.9 | 74.3 |
| Microcrystalline fenofibrate | 82.8 | 71.3 |
| Fenofibrate nanoparticulate (Tricor 145 ™ crushed tablet) | 77.2 | 54.6 |
| Example 1 (Spray-dried fenofibrate) | 81.2 | 71.8 |
| Example 2 | 78.0 | 43.9 |
| Example 3 | Non-resolved peak of fenofibrate | |
| Example 4.1 | 72.0 | 39.0 |
| Example 4.2 | 63.6 | 6.5 |
| Example 4.3 | 63.7 | 16.5 |
| Example 4.4 | 67.6 | 24.8 |
| Example 4.5 | 78.4 | 43.3 |
| Example 4.6 | 73.3 | 34.4 |
| Example 4.7 | 66.0 | 17.3 |
| Example 4.8 | 68.0 | 22.3 |
| Example 4.9 | 75.6 | 35.8 |
| Example 4.10 | 78.6 | 42.8 |
| Example 4.11 | 63.7 | 21.1 |
| Example 4.12 | 78.2 | 52.4 |
| Example 4.13 | 72.6 | 38.5 |

TABLE 3-continued

DSC of fenofibrate formulations

| Sample | $T_{melt}$ (° C.) | $\Delta H_{melt}$ (J/$g_{FF}$) |
|---|---|---|
| Example 4.14 | Non-resolved peak of fenofibrate | |
| Example 5 | 69.1 | 30.5 |
| Example 6 | 71.1 | 33.4 |
| Example 7 | 76.8 | 49.0 |
| Example 8 | 78.0 | 11.0 |
| Example 9 | 78.0 | 16.7 |

As can be seen from Table 3, raw crystalline fenofibrate powder (starting material) exhibits an endothermic peak around 82° C. with melting enthalpy 74.3 J/g. Commercial micronized (microcrystalline) fenofibrate demonstrates only a minor change of the fenofibrate melting enthalpy (71.3 J/g). Fenofibrate nanoparticulate produced by milling Tricor® 145 tablet ($\Delta H_{melt}$=54.6 J/g) shows a reduction of melting energy of only 19.7 J/g. The application of spray-drying process (Example 1) alone leaves fenofibrate almost unchanged (see also FIG. 1).

Figure 2:
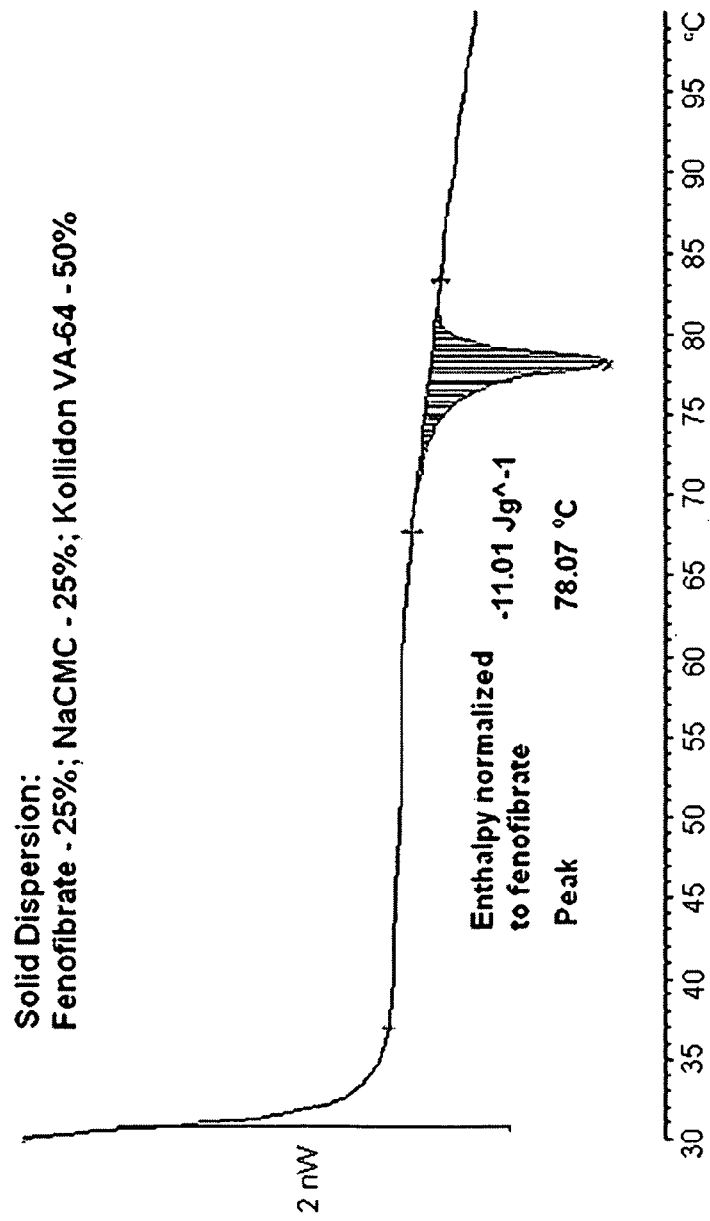
FIG. 2 depicts the Differential Scanning Calorimetry (DSC) thermogram of the fenofibrate composition according to the invention comprising Copovidone K28 and NaCMC (Example 8) as shown in Table 3 (Example 11).

In contrast, introduction of fenofibrate into the polymers-fenofibrate complex according to the invention and its interaction with hydrophobic moieties of the amphiphilic polymer resulted in a significant depression of the drug fusion peak ($\Delta H_{melt}$). The compositions described in examples 4.2, 4.3, 4.4, 4.6 to 4.9, 4.11, 5, 6, 8, and 9 demonstrate 2-10 fold reduction of enthalpy compared to bulk starting fenofibrate More specifically, FIG. 2 illustrates this phenomenon and shows 6.8-fold reduction of fenofibrate enthalpy for the solid dispersion described in Example 8.

The maximum degree of interaction between fenofibrate and Poloxamer 407 in the ratio 1:3 (Examples 3 and 4.14) results in an extremely strong depression of the melting point of fenofibrate, overlapping with the polymer peak, and thus no resolved peak of drug is observed.

Figure 3:
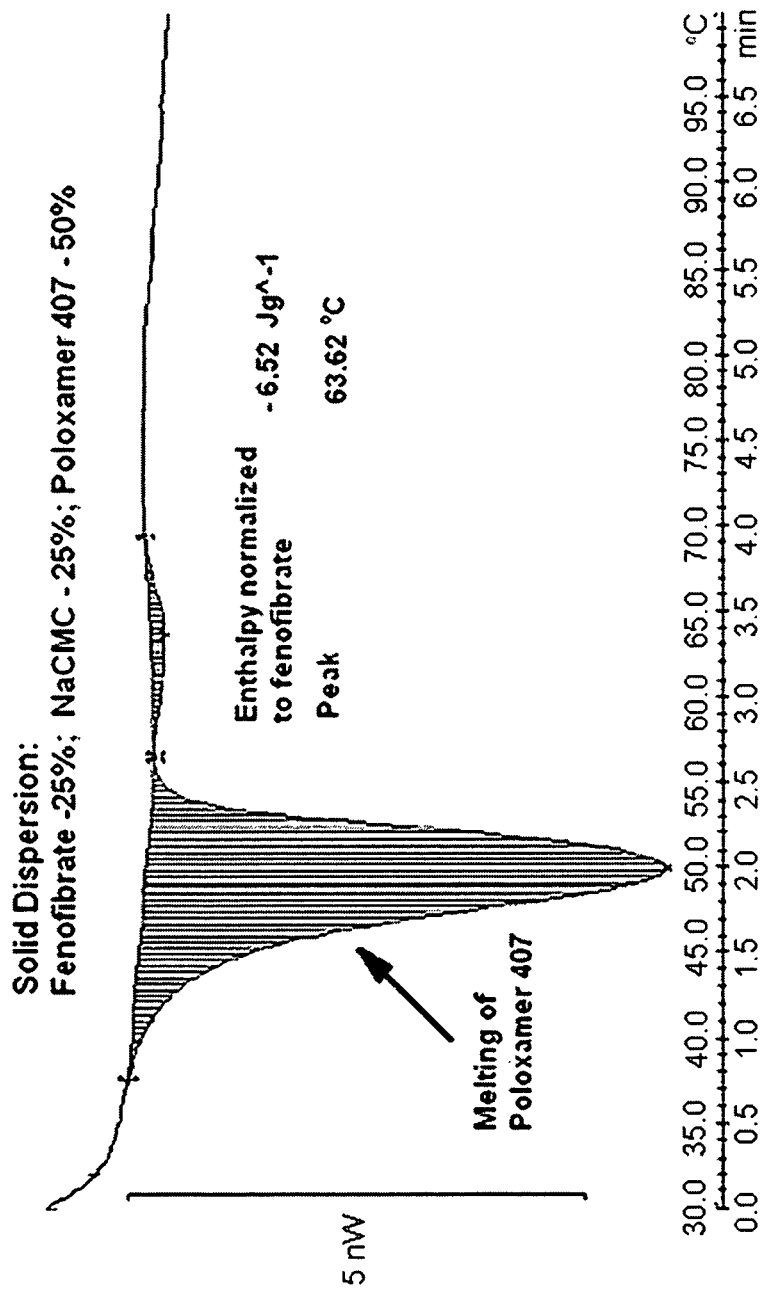
FIG. 3 depicts the Differential Scanning Calorimetry (DSC) thermogram of the fenofibrate composition according to the invention comprising Poloxamer 407 and NaCMC (Example 4.2) as shown in Table 3 (Example 11).

The thermotropic profile of the compositions of the invention also pointed out strong interactions of the fenofibrate with the polymers. The temperature of melting was shifted down from 82-83° C. to 63-73° C. in the examples 4.1 to 4.4, 4.6 to 4.8, 4.11, 4.13, 5, and 6. More specifically, FIG. 3 illustrates this phenomenon and shows an 18.3° C. down-shift of melting temperature for the solid dispersion of fenofibrate described in Example 4.2 as well as a 11.4-fold reduction of fenofibrate enthalpy compared to bulk starting fenofibrate.

Example 12

In Vivo Pharmacokinetics Study in Rats

In vivo studies were conducted for determining the bioavailability of the fenofibrate compositions of the present invention relative to the bioavailability of the commercially available micronized fenofibrate powder. The study was designed to determine the correlation between physico-chemical properties of the compositions (particle size and thermal behavior) and their bioavailability.

Preparations comprising fenofibrate formulations obtained in Examples 4.1, 4.2, 4.11, 4.12 or micronized fenofibrate were administered orally as water suspensions to male Sprague-Dawley rats (280-300 g; Harlan Inc., Israel), via a feeding tube (gavage). Water suspensions were prepared 1 hr before their administration to rats in concentration 1.5 mg/ml and pulled by a syringe at continuous mixing on a magnet stirrer. Each rat was administered a single oral dose of 7.5 mg/kg. Administration of the drug followed overnight fasting, while water was freely available. Blood samples were collected from the tail at the following points of time: pre-dosing and 1, 2, 3 and 4 hours post-dosing. Blood concentration of fenofibric acid at each point of time was determined by HPLC-UV method (materials and Methods, item ix) and calculated as average for a group of 5 animals. Pharmacokinetic parameters ($C_{max}$, $AUC_{0-4}$, $C_{maxtest}/C_{maxref}$, and $AUC_{0-4test}/AUC_{0-4ref}$) were determined for each formulation. The correlation between results and compositions are shown in Table 4.

TABLE 4

Fenofibric acid pharmacokinetic parameters in rats

| Formulation | Composition FFB:Amp:Hydro (%) | Ratio FFB:Amp | $C_{max}$ µg/ml | $AUC_{0-4}$ | $AUC_{0-4test}/AUC_{0-4ref}$ |
|---|---|---|---|---|---|
| Micronized Fenofibrate | | | 6.19 | 20.7 | |
| Example 4.1 | 25:25:50 | 1.00:1.00 | 20.09 | 54.6 | 2.64 |
| Example 4.2 | 25:50:25 | 1.00:2.00 | 20.47 | 69.2 | 3.34 |
| Example 4.11 | 33.3:44.3:22.3 | 1.00:1.33 | 10.89 | 36.8 | 1.78 |
| Example 4.12 | 33.3:22.3:44.3 | 1.00:0.67 | 7.78 | 25.5 | 1.23 |

As can be seen from Table 4, all formulations of the invention demonstrated a significantly better absorption of fenofibrate into rat blood stream than commercial micronized fenofibrate. In addition, the formulations of Examples 4.1 and 4.2 with loading of 25% fenofibrate showed better absorption ($C_{max}$=20.09, 20.47) than formulations of Examples 4.11; 4.12 with loading of 33.3% fenofibrate Poloxamer 407: NaCMC=1:2, Examples 4.1 and 4.12 or 2:1, Examples 4.2 and 4.11), the preferable ratio is 2:1, with the excess of Poloxamer 407.

These results teach that the highest bioavailability is correlated with the most significant depression of both thermal characteristics—enthalpy and temperature, as shown in Table 3 for formulation 4.2.

Example 13

Stability of Spray-Dried Powders

Samples of the spray-dried formulation of 4.2 and 4.3 were stored during twelve months (25° C. and 60% RH) and were subjected to a fenofibrate assay, water content, as well as particles size and thermal properties measurements as described in Methods. The properties of the formulations after storage were compared with the initial properties of the material. The results are summarized in Table 5.

TABLE 5

Properties of initial spray dried powders and samples after storage

| Compositions | Assay (mg/g) | Water (%) | $T_m$ (° C.) | $\Delta H_m$ (J/$g_{FFB}$) | Main peak, nm(% vol) |
|---|---|---|---|---|---|
| Example 4.2$_{initial}$ | 235.7 | 4.14 | 63.6 | 6.5 | 669 (99) |
| Example 4.2$_{stored}$ | 239.4 | 4.08 | 63.1 | 7.6 | 812 (100) |
| Example 4.3$_{initial}$ | 240.2 | 2.86 | 63.7 | 16.5 | 916 (100) |
| Example 4.3$_{stored}$ | 239.1 | 3.17 | 62.9 | 14.6 | 847 (90) |

Analysis of the obtained results reveals that the recovery of fenofibrate after storage is within 90%-110% of the assay value for the initial sample; water, fenofibrate melting point and enthalpy and data of particle size distribution of the formulations after storage differ from the initial parameters by no more than 20%. Thus, the characteristics of the spray-dried powders demonstrate that the compositions described in the Examples 4.2 and 4.3 are stable under storage at 25±2° C. and 60% RH during at least twelve months.

Example 14

Immediate Release Tablets

The powder materials of the polymers-fenofibrate compositions were blended with inactive ingredients acting as tablet fillers, diluents, disintegrants, wicking agents or lubricants. The mixtures were compressed into tablets of 145 mg strength. The compositions of tablets (A-F) and results of their dissolution tests are given in Tables 6 and 7, respectively.

TABLE 6

Compositions of the fenofibrate tablets

| Ingredient | A (mg) | B (mg) | C (mg) | D (mg) | E (mg) | F (mg) |
|---|---|---|---|---|---|---|
| Powder of Example 4.3 | 592 | 592 | 592 | 592 | 592 | 592 |
| Lactose | 200 | | | 206 | 112 | 60 |
| Dextrates | | 200 | 160 | | | |
| Sodium Starch Glycolate | | | 40 | | | |
| Calcium Silicate | | | | | 80 | 54 |
| Sodium Lauryl Sulfate | | | | | 16 | 33 |
| Sodium Docusate | | | | | | 21 |
| Sodium Benzoate | | | | | | 5 |
| Magnesium Stearate | 8 | 8 | 8 | 2 | | 2 |
| Tablet total weight (mg) | 800 | 800 | 800 | 800 | 800 | 767 |

TABLE 7

Dissolution profiles of tablets A-E in % of dissolved fenofibrate

| Minutes | A | B | C | D | E | F |
|---|---|---|---|---|---|---|
| 20 | 41.7 | 45.3 | 28.7 | 29.0 | 28.3 | 24.1 |
| 30 | 58.8 | 64.3 | 43.1 | 46.0 | 43.6 | 39.3 |
| 40 | 73.2 | 78.3 | 56.3 | 58.2 | 56.3 | 50.7 |
| 60 | 93.7 | 95.9 | 77.3 | 78.1 | 76.8 | 69.5 |

In order to predict the behavior of the tablets in vivo, disintegration tests were carried out in gastrointestinal fluids (GIF). Tablet B was placed into simulated gastric fluid (SGF, pH=1.2) for 1 h and after this into simulated intestinal fluid (SIF, pH=6.8) for additional two hours. The tablet remained intact after exposure to SGF, while in the SIF tablet disintegrated completely for 2 h. The colloidal dispersion obtained after disintegration showed the same particles size as dispersion formed by the initial powder of formulation 4.3.

Example 15

Pharmacokinetic Study of the Fenofibrate Formulations in Powder Form in Humans

A bioavailability test of the formulations 4.1 and 4.2 and Tricor® 145 mg was carried out in humans as follows. A randomized three-way crossover comparative bioavailability study was carried out with a single 145 mg dose in 12 healthy volunteers using the formulations of Examples 4.1 and 4.2 and Tricor® 145 mg. The study was done in the fasted state. The formulations 4.1 and 4.2 were administered as oral suspensions (50 ml) and Tricor® 145 mg as a tablet. A 10-day washout between periods was maintained before dosing the next product. Blood samples were collected in each period at 0, 1, 2, 3, 4, 5, 6, 7, 8, 9, 10, 12, 23, 47, 71 and 95 hours in order to characterize drug absorption and elimination. These samples were analyzed for fenofibric acid content by a HPLC-UV validated method.

The pharmacokinetic parameters of the tests of the compositions 4.1 and 4.2 of the invention and the reference product Tricor®145 absorptions are shown below in Table 8.

TABLE 8

Fenofibrate pharmacokinetic parameters in humans

| FormulaTion | $AUC_{inf}$ (μg · h/ml) | $AUC_{0-95\,h}$ (μg · h/ml) | $T_{max}$ (h) | $C_{max}$ (μg/ml) | $C_{maxtest}/C_{maxref}$ | $AUC_{inf.\,test}/AUC_{inf.\,ref}$ |
|---|---|---|---|---|---|---|
| Tricor145 ™ | 127.0 SD = 42.6 | 121.6 SD = 38.7 | 2.2 SD = 0.83 | 8.25 SD = 1.63 | | |
| Example 4.1 | 121.7 SD = 42.1 | 116.2 SD = 39.5 | 2.2 SD = 0.80 | 6.28 SD = 1.24 | 0.76 | 0.96 |
| Example 4.2 | 121.0 SD = 41.0 | 116.2 SD = 37.4 | 3.0 SD = 0.82 | 7.16 SD = 1.16 | 0.87 | 0.95 |

The pharmacokinetic parameters shown in Table 8 first demonstrate that there is no difference in the amount of drug absorbed when the suspensions of the inventions 4.1 or 4.2 are administrated versus commercial Tricor® 145 mg tablet (see AUC results). Second, the data show that the rate of fenofibrate absorbance is higher for the formulation 4.2 (87% of reference $C_{max}$ result) than for formulation 4.1 (76% of reference $C_{max}$ result).

As can be concluded from this preliminary study, the high degree of polymer-drug interactions, which express themselves in the thermal properties and ability to form the nanodispersion, are key factors that impact the rate of fenofibrate absorption. The higher $C_{max}$ result of formulation 4.2 in humans could be predicted from its physicochemical properties enabling higher absorption into the rat bloodstream.

Example 16

Combination of Fenofibrate and Aspirin in One Capsule

Method A: 590 mg of the composition described in the example 4.3 comprising 145 mg of fenofibrate was blended with 75 mg of aspirin and filled to a capsule.

Method B: 590 mg of the composition described in the example 4.3 comprising 145 mg of fenofibrate was dry granulated using a roller compactor. 75 mg of aspirin was blended with 100 mg of lactose and then dry granulated using roller compactor. Granules containing fenofibrate and granules containing aspirin were blended and filled to capsule.

Example 17

Combination of Fenofibrate and Aspirin in One Tablet

Method A: 590 mg of the composition described in the example 4.3 comprising 145 mg of fenofibrate is blended with 75 mg of aspirin, 100 mg of lactose and 8 mg of magnesium stearate and compressed to tablet.

Method B: 590 mg of the composition described in the example 4.3 comprising 145 mg of fenofibrate is dry granulated using roller compactor. 75 mg of aspirin is blended with 100 mg of lactose and 8 mg of magnesium stearate and the mixture is dry granulated using roller compactor. Granules containing fenofibrate and granules containing aspirin are blended and compressed to tablet.

Method C: Granules containing fenofibrate (145 mg) obtained according to the method B are filled to the tablet mold as the first layer and then granules containing aspirin (75 mg) obtained according to the method B are filed to the tablet mold as the second layer. The two tablet layers are compressed using appropriate conventional tools and a suitable bilayer tabletting press, to form a bilayered tablet.

Example 18

Spray-Dried Atorvastatin 0.3 g of Atorvastatin was dissolved under stirring at 300 rpm in a mixture of 21.6 g n-propanol and 17 g water at 40° C. The resultant clear homogeneous solution was placed to the bath at 55° C. and spray dried, using Buchi Mini Spray Drier with inlet air temperature 108° C. and outlet temperature 71° C., thus obtaining a powder. This powder was suspended in deionized water as described in the Method section, item (vii), and formed coarse suspensions with large visible particles. This kind of suspension is unsuitable for Dynamic Light Scattering measurement.

No atorvastatin melting peak was found on the DSC thermogram after preparation, confirming an amorphous form of the drug. However, after storage of six months some broad peak in the range of 116-183° C. appeared. This peak can be attributed to the beginning of the crystallization process.

Example 19

Atorvastatin Formulation Containing Poloxamer 407 and NaCMC

Drug Solution:
Atorvastatin (0.5 g) was dissolved in 48 g of 1-methyl-2-pyrrolidone at ambient conditions by stirring at 300 rpm.
Polymers Solution:
NaCMC (1.0 g) and Lutrol 127F (0.5 g) were dissolved by stirring at 300 rpm in water (50 g) at 38° C.

The drug solution was added to the polymers solution at a feeding rate of 10 ml/min, under stirring at 300 rpm at 38° C. The resultant clear homogeneous solution was spray dried using Buchi Mini Spray Drier inlet air temperature 110° C. and outlet temperature 69° C., yielding a powder, which readily dissolves in water media. No atorvastatin melting peak was found on the DSC thermogram. The thermogram of the formulation stored for six months showed the same result. A dissolution test showed that 85% of atorvastatin is released to phosphate-buffered saline (PBS), pH=6.9, during 14 min.

Example 20

Atorvastatin Formulation Containing Poloxamer 407 and Sodium Alginate

Solution A: 0.120 g Atorvastatin was dissolved in a mixture of 16 g 1-propanol and 5 ml water at 65° C., under stirring at 300 rpm, followed by addition of 0.05 g Lutrol under stirring.

Solution B: 0.300 g Sodium alginate (Protanal SF) was mixed with 3.2 g 1-propanol at ambient conditions by stirring at 300 rpm. Then, 35 g water was added under stirring and the mixture was heated up to 65° C. until full dissolution of the polymer.

Solution A was added to solution B at a feeding rate of 10 ml/min, under stirring at 500 rpm and at a temperature of 65° C. To the obtained clear viscous solution (122 csp), 20 ml n-propanol and 28 ml water were added. The resultant clear homogeneous solution was spray dried using Buchi Mini Spray Drier with inlet air temperature 115° C. and outlet temperature 70° C., yielding a powder of polymers-atorvastatin complex comprising amorphous atorvastatin and freely dissolvable in water. No atorvastatin melting peak was found on the DSC thermogram. The thermogram of the formulation stored for six months showed the same result. A dissolution test showed that 91% of atorvastatin is released to PBS, pH=6.9, during 30 min.

Example 21

Fenofibrate/Atorvastatin Formulations Containing Poloxamer 407 and NaCMC

General Procedure for Preparation of the Formulations 21.1-21.3
Drug Solution:
Appropriate amounts of fenofibrate and atorvastatin calcium (see Table 9) were dissolved in 48 g 1-methyl-2-pyrrolidone at ambient conditions.
Polymers Solution:
Appropriate amounts of NaCMC and of Poloxamer 407 (see Table 9) were dissolved by stirring at 300 rpm in 50 g water at 45° C.

The drug solution was added to hot polymers solution (68° C.) with feeding rate 2 ml/min under stirring at 300 rpm. The resulting transparent hot (68° C.) solutions were spray dried using Buchi Mini Spray Drier with inlet air temperature 110° C. and outlet temperature 70° C., producing the powders, which upon contact with water converted to colloidal dispersion.

General Procedure for Preparation Formulation 21.4 and 21.5

Drug Solution:

Appropriate amounts of atorvastatin calcium ware dissolved in a mixture of 22.5 g of n-propanol-water (44:56/v:v) at 50-60° C. under stirring at 300 rpm, followed by addition of appropriate amounts of fenofibrate to the mixture.

Polymers Solution:

Appropriate amounts of NaCMC were dissolved in 25 g water at 50-60° C. under stirring at 300 rpm, followed by addition of appropriate amounts of Poloxamer 407. In the next step, 20 g n-propanol were added to the water solution of the polymers and the mixture was heated to 70° C.

The hot (60° C.) drug solution was added to hot polymers solution (70° C.) with feeding rate 2 ml/min under stirring at 300 rpm. The resulting transparent hot (70° C.) solutions were spray dried using Buchi Mini Spray Drier with inlet air temperature 110° C. and outlet temperature 66° C. producing the powders, which upon contact with water converted to colloidal dispersion.

Table 9 presents the compositions of five different formulations of fenofibrate and atorvastatin in NaCMC and Poloxamer 407 and Table 10 presents the particle size of the water dispersions obtained from the five formulations.

TABLE 9

Composition of formulations of fenofibrate/atorvastatin containing Poloxamer 407 and NaCMC

| Formulation | Fenofibrate (g) | Atorvastatin (g) | NaCMC (g) | Lutrol (g) |
|---|---|---|---|---|
| Example 21.1 | 0.435 | 0.119 | 1.110 | 0.555 |
| Example 21.2 | 0.435 | 0.060 | 0.990 | 0.495 |
| Example 21.3 | 0.435 | 0.030 | 0.930 | 0.465 |
| Example 21.4 | 0.435 | 0.030 | 0.465 | 0.930 |
| Example 21.5 | 0.435 | 0.119 | 0.555 | 1.110 |

TABLE 10

Characteristics of the fenofibrate/atorvastatin formulations

| Formulation | Number of measurements | z-vol of the main fraction, nm | PDI | % vol of the main fraction |
|---|---|---|---|---|
| Example 21.1 | 10 | 1157 | 0.660 | 100 |
| Example 21.2 | 12 | 919 | 0.624 | 100 |
| Example 21.3 | 5 | 1694 | 0.324 | 70 |
| Example 21.4 | 5 | 645 | 0.308 | 100 |
| Example 21.5 | 5 | 1856 | 0.216 | 100 |

The results show that all powder formulations 21.1-21.5 can give colloidal dispersions in the range 600-2000 nm upon contact with water, but only compositions 21.2 and 21.4 provide nanosized particles.

Example 22

Thermal Properties of Fenofibrate/Atorvastatin Formulations

In order to determine the thermal properties of the compositions of the invention comprising fenofibrate and atorvastatin, the temperature and the enthalpy of melting of spray-dried powders were determined by Differential Scanning Calorimetry (DSC) as described in Methods section. These characteristics were compared to thermograms of starting commercial raw fenofibrate as well as of commercial fenofibrate drug products. The results are shown in Table 11. The thermograms of the combined drug formulation show no peak of atorvastatin. The enthalpy of fenofibrate melting is given in Joule per gram (J/g) of fenofibrate.

TABLE 11

DSC of fenofibrate/atorvastatin formulations

| Sample | $T_{melt}$ (° C.) | $\Delta H_{melt}$ (J/g) |
|---|---|---|
| Fenofibrate starting material | 81.9 | 74.3 |
| Microcrystalline fenofibrate | 82.8 | 71.3 |
| Fenofibrate nanoparticulate (Tricor 145 ™ crushed tablet) | 77.2 | 54.6 |
| Example 1 (Spray-dried fenofibrate) | 81.2 | 71.8 |
| Example 21.1 | 61.9 | 16.0 |
| Example 21.2 | 69.9 | 29.7 |
| Example 21.3 | 64.9 | 19.4 |
| Example 21.4 | 70.9 | 4.30 |
| Example 21.5 | 60.1 | 2.85 |

As can be seen from Table 11, the starting raw crystalline fenofibrate powder exhibits an endothermic peak around 82° C. with melting energy 74.3 μg. Commercial microcrystalline fenofibrate demonstrates only some minor changes of the fenofibrate melting enthalpy (71.3 J/g). Nanoparticulate of fenofibrate produced by milling (Tricor® 145) shows reduction of melting energy only of 19.7 μg. By applying the spray-drying process alone (Example 1), the characteristics of fenofibrate remain almost unchangeable. In contrast, the introduction of fenofibrate into the polymer(s)-fenofibrate/atorvastatine complex according to the invention and their interaction with hydrophobic moieties of the amphiphilic polymer result in a significant depression of the fenofibrate fusion peak. Pharmaceutical compositions described in examples 21.1-21.5 demonstrate 2-19 folds reduction of enthalpy compared with initial fenofibrate. The thermotropic profile of solids in these examples also pointed out strong interactions of the fenofibrate with the polymers. The temperature of melting is shifted down from 82-83° C. to 60-71° C.

Thus, it can be concluded that for compositions comprising a combination of two lipophilic drugs, each lipophilic compound demonstrates the same thermal properties as in a composition comprising the individual drugs. (Examples 11 and 19)

Example 23

Itraconazole Formulation Containing Poloxamer 407 and Chitosan

Solution A: Itraconazole (0.2 g) was dissolved in 15.2 g 1-propanol at 65° C. under stirring at 300 rpm. Then 5 g water and 0.25 g Lutrol 127F were added while stirring.

Solution B: Chitosan.HCl (0.350 g) was mixed with 2.4 g 1-propanol, 15 g water were added while stirring, and the mixture was heated up to 60° C. until full dissolution of the polymer.

Solution A was added to solution B at a feeding rate of 10 ml/min, under stirring at 500 rpm and at a temperature of 60° C. The resultant solution was spray dried using Buchi Mini Spray Drier with inlet air temperature 115° C. and outlet temperature 70° C., thus yielding a powder, which upon contact with water converted to a colloidal dispersion with a particles size of 655 nm.

Raw itraconazole crystalline powder exhibits an endothermic peak around 169.7° C. with melting energy of 84.4 J/g. In the DSC thermogram of this example, the melting temperature of itraconazole was observed at 159.0° C. and the melting enthalpy was 42.5 J/g. In the thermogram of the formulation stored for six months, the melting temperature of itraconazole was observed at 158.4° C. and the melting enthalpy was 42.5 J/g.

Example 24

Itraconazole Formulation Containing Poloxamer 407 and NaCMC

Drug Solution:
Itraconazole (0.5 g) was dissolved in 39 g acetonitrile and 3 g acetic acid at 60° C. under stirring at 300 rpm.
Polymers Solution:
NaCMC (0.5 g) and Lutrol 127F (1.0 g) were dissolved under stirring at 300 rpm in water (45 g) at 55° C.

The drug solution was added to the polymers solution at a feeding rate of 10 ml/min, under stirring at 300 rpm at 65° C. The resulting transparent solution was spray dried using Buchi Mini Spray Drier with inlet air temperature 125° C. and outlet temperature 79° C., thus yielding a free-flowing powder comprising 2-10 μm particles, which upon contact with water converted to colloidal dispersion with a particles size of 1108 nm.

Raw itraconazole crystalline powder exhibits an endothermic peak around 169.7° C. with melting energy of 84.4 J/g. In the DSC thermogram of this example, the melting temperature of itraconazole was observed at 155.6° C. and the melting enthalpy was 21.9 J/g. In the thermogram of the formulation stored for six months, the melting temperature of itraconazole was observed at 154.4° C. and the melting enthalpy was 24.6 J/g.

Example 25

Itraconazole Formulation Containing PVP and Corn Zein

Solution A:
Itraconazole (0.20 g) and 0.2 g corn zein were dissolved in a mixture of 18 g 1-propanol and 2.5 g water at 60° C., under stirring at 300 rpm.
Solution B:
0.1 g PVP (Kollidon® 30, BASF) was dissolved in 20 g deionized water under stirring at 300 rpm and the mixture was heated up to 60° C. until full dissolution of the polymer.

The solution A was added to solution B at a feeding rate of 10 ml/min, under stirring at 500 rpm, at 60° C. The obtained warm (52° C.) opalescent homogeneous solution was spray dried using Buchi Mini Spray Drier with inlet temperature 80° C. and outlet temperature 53° C., thus yielding off-white powder comprising 2-10 μm particles, which upon contact with water converted to colloidal dispersion with a particles size of 919 nm.

No itraconazole melting peak was found on the DSC thermogram. The thermogram of the formulation stored for six months showed the same result.

Example 26

Dissolution Profile of Itraconazole

Portions of spray-dried powders obtained in Examples 23-25 as well as control powders containing 100 mg itraconazole were dissolved in 900 ml of a 0.05 M solution of sodium lauryl sulfate, at 37° C., at a rotation speed of 100 rpm and sampling time of 10, 30, 60 and 90 min.

The dissolution profiles of itraconazole are reported in Table 12. As can be seen, the itraconazole compositions of Examples 24 and 25 showed significantly more rapid dissolution as compared to raw itraconazole material. The dissolution of these compositions was similar to itraconazole from Sporanox™ granules.

TABLE 12

| Dissolution profile in % of dissolved itraconazole | | | | |
|---|---|---|---|---|
| Sample | 10 min | 30 min | 60 min | 90 min |
| Itraconazole raw powder | 7.8 | 23.2 | 35.9 | 44.5 |
| Sporanox ™ | 64.0 | 100.0 | 100.0 | 100.0 |
| Example 23 | 10.0 | 37.3 | 58.6 | 63.7 |
| Example 24 | 57.6 | 73.4 | 75.7 | 80.5 |
| Example 25 | 70.8 | 75.4 | 77.2 | 80.9 |

Example 27

Tacrolimus Formulation Containing Poloxamer 407 and NaCMC

Drug Solution:
Tacrolimus (0.09 g) was dissolved in 8 gl n-propanol at ambient conditions by stirring at 300 rpm.
Polymers Solution:
NaCMC (0.09 g) and Lutrol 127F (0.18 g) were dissolved by stirring at 300 rpm in water (10 g) at 40° C.

The drug solution was added to the polymers solution at a feeding rate of 2 ml/min, under stirring at 300 rpm at 45° C. The resultant clear homogeneous solution was dried using Buchi rotavapor, thus yielding a powder that upon contact with water converted to colloidal dispersion with a particles size of 910 nm.

Raw tacrolimus crystalline powder exhibits an endothermic peak around 135.3° C. with melting energy of 60.1 J/g. In the DSC thermogram of this example, the melting temperature of tacrolimus was observed at 118.5° C. and the melting enthalpy was 52.2 J/g.

Example 28

Nifedipine Formulation Containing Poloxamer 407 and NaCMC

Drug Solution:
Nifedipine (0.50 g) was dissolved in 40 g n-propanol at ambient conditions by stirring at 300 rpm.
Polymers Solution:
NaCMC (0.50 g) and Lutrol 127F (1.00 g) were dissolved by stirring at 300 rpm in 50 g water at 45° C.

The drug solution was added to the polymers solution at a feeding rate of 2 ml/min, under stirring at 300 rpm at 55° C. The resultant clear homogeneous solution was spray dried using Buchi spray drier thus yielding a powder, which upon contact with water converted to a colloidal dispersion with a particles size of 1190 nm.

Raw nifedipine crystalline powder exhibits an endothermic peak around 172.4° C. with melting energy of 113.4 J/g. In the DSC thermogram of this example, the melting temperature of nifedipine was observed at 140.9° C. and the melting enthalpy was 8.4 J/g.

Example 29

Clarithromycin Formulation Containing Poloxamer 407 and NaCMC

Drug Solution:
Clarithromycin (0.50 g) was dissolved in 40 g n-propanol at 35° C. by stirring at 300 rpm.
Polymers Solution:
NaCMC (0.50 g) and Lutrol 127F (1.00 g) were dissolved by stirring at 300 rpm in water (50 g) at 45° C.
The drug solution was added to the polymers solution at a feeding rate of 2 ml/min, under stirring at 300 rpm at 57° C. The resultant clear homogeneous solution was dried using Buchi spray drier thus yielding a powder, which upon contact with water convered to colloidal dispersion with a particles size of 836 nm.
Raw clarithromycin crystalline powder exhibits an endothermic peak around 227.6° C. with melting energy of 70.2 J/g. In the DSC thermogram of this example, the melting temperature of clarithromycin was observed at 207.9° C. and the melting enthalpy was 40.1 J/g.

Example 30

Albendazole Formulation Containing Poloxamer 407 and NaCMC

Drug Solution:
Albendazole (0.50 g) was dissolved in 44.5 g tetrahydrofuran at 35° C. by stirring at 300 rpm.
Polymers Solution:
NaCMC (0.50 g) and Lutrol 127F (1.00 g) were dissolved by stirring at 300 rpm in water (50 g) at 45° C.
The drug solution was added to the polymers solution at a feeding rate of 2 ml/min, under stirring at 300 rpm at 38° C. The resultant clear homogeneous solution was dried using Buchi spray drier thus yielding a powder, which upon contact with water converted to colloidal dispersion with a particles size of 555 nm.
Raw albendazole crystalline powder exhibits an endothermic peak around 215° C. with melting energy of 209.7 J/g. In the DSC thermogram of this example, the melting temperature of albendazole was observed at 161.1° C. and the melting enthalpy was 31.2 J/g.
The formulation of this example demonstrated significantly higher dissolution rate in 0.05 M sodium lauryl sulfate than that of raw albendazole: 73.2% of formulated albendazole was dissolved after 15 min, while only 16.6% of raw material was released at the same point of time.

Example 31

Pharmacokinetic Study of Formulated Albendazole Oral Suspension in Pigs

A randomized four-way parallel comparative bioavailability study was carried out with a single administration of two dose level (5 mg/kg and 10 mg/kg) using the formulation of Example 30 and the commercial veterinary drug Albazen containing the same active compound in groups of 5 pigs (20 kg). The study was done in the fasted state. All formulations were administered as oral suspensions (2 and 4 ml). Blood samples were collected in each period at 0, 3, 9 and 24 hours in order to characterize drug absorption and elimination. These samples were analyzed for albendazole sulfoxide content by a HPLC-UV validated method.

Figure 4:
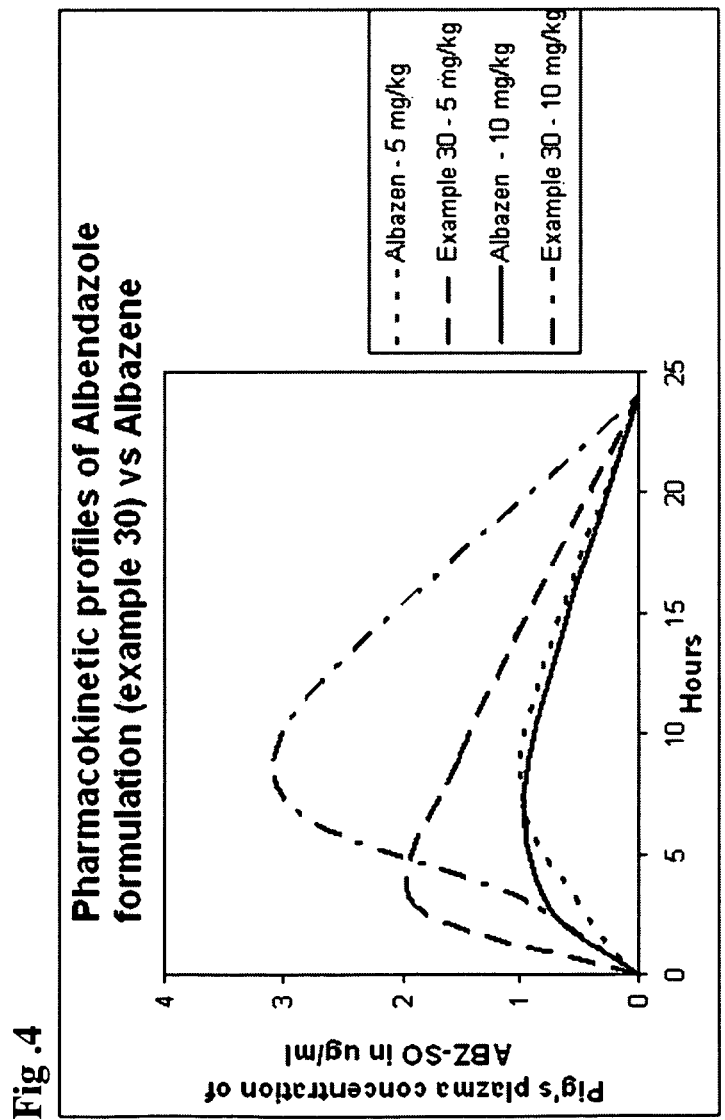
FIG. 4 depicts the pharmacokinetic profile of albendazole formulation, Example 30, vs. a commercial albendazole product (Albazen).

Pharmacokinetic parameters ($C_{max}$, $AUC_{0-24}$, $C_{max\ test}/C_{max\ ref}$ and $AUC_{0-24test}/AUC_{0-24ref}$) were determined for each formulation. The results are shown in Table 13 and FIG. 4.

TABLE 13

Albendazole-SO pharmacokinetic parameters in pigs

| Formulation | $C_{max}$ µg/ml | $AUC_{0-24}$ µg · h/ml | $C_{max\ test}/C_{max\ ref}$ | $AUC_{0-24test}/AUC_{0-24ref}$ |
|---|---|---|---|---|
| Albazen (5 mg/kg) | 0.98 | 12.54 | | |
| Example 30 (5 mg/kg) | 1.91 | 24.66 | 1.95 | 1.97 |
| Albazen (10 mg/kg) | 0.92 | 13.13 | | |
| Example 30 (10 mg/kg) | 3.08 | 36.45 | 3.35 | 2.77 |

Example 32

Fenbendazole Formulation Containing Poloxamer 407 and NaCMC

Drug Solution:
Fenbendazole (0.25 g) was dissolved in 22.5 g of dimethyl sulfoxide at ambient conditions by stirring at 300 rpm.
Polymers Solution:
NaCMC (0.25 g) and Lutrol 127F (0.50 g) were dissolved by stirring at 300 rpm in water (25 g) at 40° C.
The drug solution was added to the polymers solution at a feeding rate of 2 ml/min, under stirring at 300 rpm at 80° C. The resultant clear homogeneous solution was dried using Buchi spray drier thus yielding a powder, which upon contact with water converted to a colloidal dispersion with a particles size of 892 nm.
Raw fenbendazole crystalline powder exhibits an endothermic peak around 239° C. with melting energy of 166.3 J/g. In the DSC thermogram of this example, the melting temperature of fenbendazole was observed at 203.7° C. and the melting enthalpy was 8.9 J/g.

Example 33

Hesperetin Formulation Containing Poloxamer 407 and NaCMC

A mixture of NaCMC (1.5 g) and Lutrol 127F (3 g) was dissolved by stirring at 300 rpm in water (64 g) at ambient conditions, followed by addition of ethanol (44 g). Hesperetin (1.5 g) was added to the polymers solution and this mixture was heated up to 64° C. until full dissolution of hesperetin. The resultant clear homogeneous solution was dried using Buchi spray drier thus yielding a powder, which upon contact with water converted to a colloidal dispersion with a particles size in nanoscale range.
Raw hesperetin crystalline powder exhibits an endothermic peak around 231° C. with melting energy of 166.2 J/g. In the DSC thermogram of this example, no peak was observed which could correspond to hesperetin.

Example 34

Resveratrol Formulation Containing Poloxamer 407 and NaCMC

Drug Solution:
Resveratrol (1.5 g) was dissolved in 32 g ethanol at ambient conditions by stirring at 300 rpm.

Polymers Solution:

NaCMC (1.5 g) and Lutrol 127F (3.0 g) were dissolved by stirring at 300 rpm in water (64 g) at ambient conditions.

The drug solution was added to the polymers solution at a feeding rate of 2 ml/min, under stirring at 300 rpm at 60° C. The resultant clear homogeneous solution was dried using Buchi spray drier thus yielding a powder, which upon contact with water converted to colloidal dispersion with a particles size in nanoscale range.

Raw resveratrol crystalline powder exhibits an endothermic peak of 267.4° C. with melting energy of 253.6 J/g. In the DSC thermogram of this example, the melting temperature of resveratrol was observed at 201.2° C. and the melting enthalpy was 12.4 J/g.

Example 35

Resveratrol Formulation Containing Poloxamer 407 and Sodium Alginate

Solution A:

Resveratrol (1.5 g) was dissolved in 23.4 g ethanol at ambient conditions under stirring at 300 rpm. Then 5 g water and 3 g Poloxamer 407 were added under stirring and all solids were dissolved.

Solution B:

Sodium alginate (1.5 g) was mixed with 8.8 g ethanol at ambient conditions under stirring at 300 rpm. Then 59 g water were added under stirring and the mixture was heated up to 68° C. until full dissolution of polymer.

Solution A was added to solution B at a feeding rate of 2 ml/min under stirring conditions (300 rpm) and at temperature 60° C. The resultant clear homogeneous solution was spray dried using Buchi Mini Spray Drier with inlet air temperature 90° C. and outlet temperature 64° C., thus obtaining a powder, which upon contact with water converted to colloidal dispersion with a particles size in nanoscale range.

Raw resveratrol crystalline powder exhibits an endothermic peak of 267.4° C. with melting energy of 253.6 J/g. In the DSC thermogram of this example, the melting temperature of resveratrol was observed at 202.8° C. and the melting enthalpy was 12.9 J/g.

Example 36

Dissolution of Resveratrol Raw Powder and Resveratrol Formulations in Model Fasted Duodenal Solution The Model Fasted Duodenal Solution (MFDS) was prepared as follows: a mixture of sodium chloride (3.093 g), sodium hydrophosphate (1.719 g) and sodium taurocholate (0.8065 g) was dissolved in deionized water (300 g) using ultrasonic bath. Lecithin (0.2925 g) was dissolved in 2 ml methylene chloride and added to the buffered solution of sodium taurocholate. The resulting emulsion was stirred for 5 min and then methylene chloride was evaporated under vacuum. The obtained clear micellar solution was adjusted to the volume of 500 ml by deionized water.

For the test procedure, the test resveratrol formulations or raw resveratrol powder (10 mg) were placed into 2 ml microcentrifuge tube and MFDS (1.8 ml) was added to the each tube. The tubes were gently shaken (about 50 rpm) at 37° C. and samplings were taken at 10, 20, 40, 60 and 120 min. For this purpose, the tubes were vortexed at the highest speed for 60 seconds and then centrifuged at 13 000 G for 60 seconds. The solid-free supernatant (0.4 ml) was mixed with 0.4 ml diluent (30% water adjusted to pH 2.5 with phosphoric acid and 70% acetonitrile) and this solution was inserted into an HPLC instrument for determination of resveratrol concentration.

Figure 5:
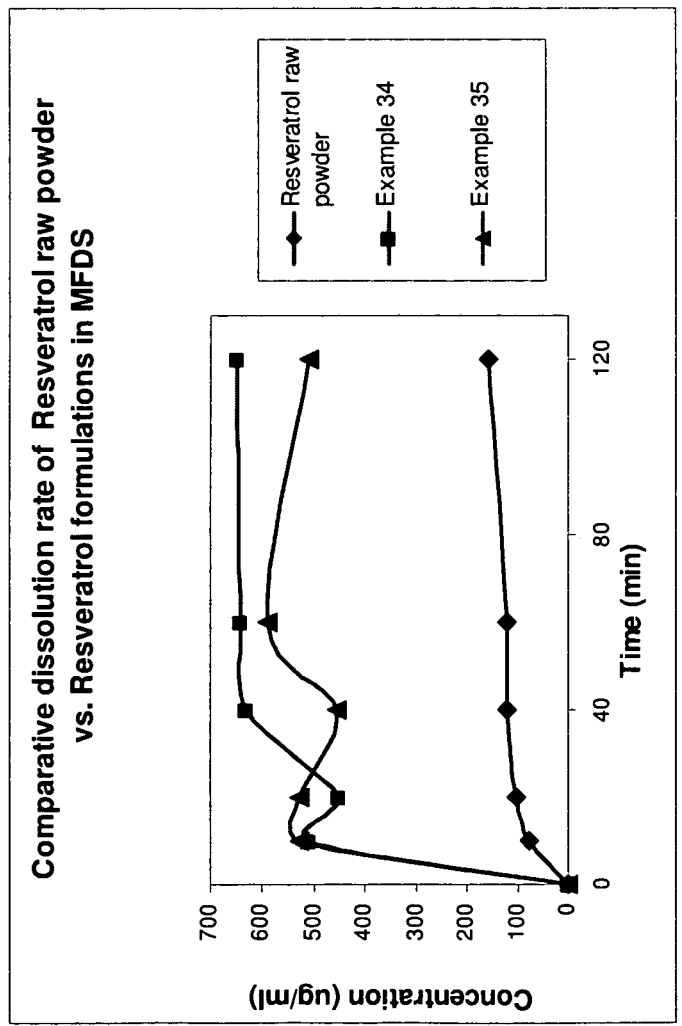
FIG. 5 depicts the comparative dissolution rate of resveratrol raw powder vs. the resveratrol formulations comprising Poloxamer 407 and NaCMC or Poloxamer 407 and sodium alginate (Examples 34-35) in the model fasted duodenal solution

The results of dissolution of raw resveratrol and resveratrol formulations in MFDS are summarized in Table 13 and in FIG. 5.

TABLE 13

Comparative dissolution rate of resveratrol raw powder vs. resveratrol formulations in MFDS

| Sample | Concentration of resveratrol (µg/ml) | | | | |
| --- | --- | --- | --- | --- | --- |
| | 10 min | 20 min | 40 min | 60 min | 120 min |
| Resveratrol raw powder | 76.65 | 103.15 | 119.3 | 121.05 | 155.6 |
| Example 34 | 510.7 | 451.9 | 630.4 | 641.2 | 647.4 |
| Example 35 | 529.05 | 529 | 454.1 | 589.9 | 511.7 |

This example clearly confirms that formulated resveratrol has high dissolution rate and saturated solubility as compared to raw resveratrol powder.

Example 37

Pharmacokinetic Study of the Resveratrol Formulations in Powder Form in Humans

A randomized two-way crossover comparative bioavailability study was carried out with a single 500 mg dose using the formulation of Example 35 and raw resveratrol powder in 12 healthy volunteers. The study was done in the fasted state. The formulations 35 and raw resveratrol powder were administered as oral suspensions ml). A 7-day washout between periods was maintained before dosing the next product. Blood samples were collected in each period at 0, 0.5, 1, 1.5, 2, 3, 4, 5, 6, 7, 8, 10, 12, 23 and 36 hours in order to characterize drug absorption and elimination. These samples were analyzed for resveratrol and its metabolites content by a HPLC-UV validated method.

The invention claimed is:

1. A solid composition formulated into a dosage form for oral administration selected from the group consisting of capsules, tablets, beads, grains, pills, granulates, granules, powder, pellets, sachets, troches, oral suspensions and aerosol, the composition comprising at least one crystalline lipophilic active compound and two or more polymers, in which the at least one lipophilic active compound is interwoven with a polymeric matrix formed by the two or more polymers, wherein at least one of the two or more polymers is an amphiphilic polymer and at least another of the two or more polymers is either a hydrophilic polymer or an amphiphilic polymer with a hydrophobic-hydrophilic balance different from the first amphiphilic polymer, such that the composition possesses a hydrophobic-hydrophilic gradient, wherein the composition does not include a solid solution of lipophilic active compound and wherein each of the at least one lipophilic active compound has modified physico-chemical properties, such that the lipophilic active compound in the composition has an enthalpy of melting and a temperature of melting, the enthalpy of melting being decreased as compared to the same bulk starting crystalline lipophilic active compound or both the enthalpy of melting and the temperature of melting being decreased as compared to the same bulk starting crystalline lipophilic active compound, and wherein said polymeric matrix is not crosslinked and no covalent interaction occurs between the two or more polymers and between the polymers and the at least one lipophilic active compound, whereby said composition permits immediate release and high bioavailability of the at least one lipophilic active compound.

2. The composition according to claim 1, wherein said amphiphilic polymer is selected from the group consisting of polyethylene oxide (PEO), PEO derivatives, poloxamers, poloxamines, polyvinylpyrrolidones, hydroxypropyl cellulose, hypromellose, hypromellose phthalate, hypromellose acetate succinate, polyacrylates, polymethacrylates, polyethylene glycol (PEG) copolymers, PEO/polypropylene glycol copolymers, PEG-modified starches, vinyl acetate-vinyl pyrrolidone copolymers, polyacrylic acid copolymers, polymethacrylic acid copolymers, plant proteins and protein hydrolysates.

3. The composition according to claim 1, wherein said hydrophilic polymer is selected from the group consisting of starch, sodium carboxymethylcellulose, hydroxyethylcellulose, polyvinyl alcohol, sodium alginate, chitosan, and carrageenan.

4. The composition according to claim 1, wherein two polymers form the polymeric matrix, one of the polymers is an amphiphilic polymer and the other polymer is a hydrophilic polymer, said polymeric matrix is not crosslinked and no covalent interaction occurs between the two polymers.

5. The composition according to claim 4, wherein the amphiphilic polymer is Poloxamer 407 or vinylpyrrolidone-vinyl acetate copolymer, and the hydrophilic polymer is sodium carboxymethylcellulose, sodium alginate or chitosan.

6. The composition according to claim 1, wherein two amphiphilic polymers form the polymeric matrix, said polymeric matrix is not crosslinked and no covalent interaction occurs between the two polymers.

7. The composition according to claim 6, wherein the two amphiphilic polymers are polyvinylpyrrolidone and a plant protein, or hypromellose acetate succinate and protein hydrolysate.

8. The composition according to claim 1, wherein three polymers form the polymeric matrix, one of the three polymers is an amphiphilic polymer and the other two polymers are hydrophilic polymers, said polymeric matrix is not crosslinked and no covalent interaction occurs between the two polymers.

9. The composition according to claim 1, wherein three polymers form the polymeric matrix, two of the three polymers are amphiphilic polymers with different hydrophobic-hydrophilic balance and the third polymer is a hydrophilic polymer, said polymeric matrix is not crosslinked and no covalent interaction occurs between the two polymers.

10. The composition according to claim 9, wherein the two amphiphilic polymers are polyvinylpyrrolidone and a plant protein hydrolysate or polyvinylpyrrolidone and Poloxamer 407 and the hydrophilic polymer is sodium carboxymethylcellulose.

11. The composition according to claim 1, which is a pharmaceutical composition wherein said at least one lipophilic active compound is at least one lipophilic drug, and wherein said polymeric matrix is not crosslinked and no covalent interaction occurs between the two or more polymers and between the polymers and the at least one lipophilic drug.

12. The pharmaceutical composition according to claim 11, wherein said at least one lipophilic drug is fenofibrate, atorvastatin, clarithromycin, itraconazole, nifedipine, albendazole, or tacrolimus.

13. The pharmaceutical composition according to claim 12, comprising fenofibrate as the sole lipophilic drug.

14. The pharmaceutical composition according to claim 13, comprising fenofibrate and two polymers forming the polymeric matrix, wherein one of the polymers is an amphiphilic polymer and the other polymer is a hydrophilic polymer.

15. The pharmaceutical composition according to claim 14, wherein the amphiphilic polymer is Poloxamer 407 and the hydrophilic polymer is either sodium carboxymethylcellulose or sodium alginate.

16. The pharmaceutical composition according to claim 15, comprising about 5%-50% by weight of fenofibrate, about 10%-60% by weight of Poloxamer 407 and about 10%-60% by weight of sodium carboxymethylcellulose or sodium alginate.

17. The pharmaceutical composition according to claim 16, comprising about 15%-35% by weight of fenofibrate, about 25%-50% by weight of Poloxamer 407 and about 25%-50% by weight of sodium carboxymethylcellulose.

18. The pharmaceutical composition according to claim 13, comprising fenofibrate and three polymers forming the polymeric matrix, wherein one of the three polymers is an amphiphilic polymer and the other two polymers are hydrophilic polymers.

19. The pharmaceutical composition according to claim 18, comprising fenofibrate and three polymers forming the polymeric matrix, wherein two of the three polymers are amphiphilic polymers with different hydrophobic-hydrophilic balance and the third polymer is a hydrophilic polymer.

20. The pharmaceutical composition according to claim 19, wherein the two amphiphilic polymers are polyvinylpyrrolidone and a plant protein hydrolysate and the hydrophilic polymer is sodium carboxymethylcellulose.

21. The pharmaceutical composition according to claim 12, comprising atorvastatin as the sole lipophilic drug.

22. The pharmaceutical composition according to claim 21, comprising atorvastatin and two polymers forming the polymeric matrix, wherein one of the polymers is an amphiphilic polymer and the other polymer is a hydrophilic polymer.

23. The pharmaceutical composition according to claim 22, wherein the amphiphilic polymer is Poloxamer 407 and the hydrophilic polymer is either sodium carboxymethylcellulose or sodium alginate.

24. The pharmaceutical composition according to claim 23, comprising about 5%-50% by weight of atorvastatin, about 10%-60% by weight of Poloxamer 407 and about 10%-60% by weight of sodium carboxymethyl-cellulose or sodium alginate.

25. The pharmaceutical composition according to claim 12, comprising itraconazole as the sole lipophilic drug.

26. The pharmaceutical composition according to claim 25, comprising itraconazole and two polymers forming the polymeric matrix, wherein one of the polymers is an amphiphilic polymer and the other polymer is a hydrophilic polymer.

27. The pharmaceutical composition according to claim 26, wherein the amphiphilic polymer is Poloxamer 407 and the hydrophilic polymer is sodium carboxymethylcellulose, sodium alginate or chitosan.

28. The pharmaceutical composition according to claim 27, comprising about 5%-50% by weight of itraconazole, about 10%-60% by weight of Poloxamer 407 and about 10%-60% by weight of sodium carboxymethyl-cellulose, sodium alginate or chitosan.

29. The pharmaceutical composition according to claim 25, comprising itraconazole and two amphiphilic polymers forming the polymeric matrix.

30. The pharmaceutical composition according to claim 29, wherein the two amphiphilic polymers are polyvinylpyrrolidone and a plant protein.

31. The pharmaceutical composition according to claim 12, comprising tacrolimus, nifedipine, clarithromycin, or albendazole as the sole lipophilic drug and two polymers forming the polymeric matrix, wherein one of the polymers is an amphiphilic polymer, and the other polymer is a hydrophilic polymer.

32. The composition according to claim 1, which is a veterinary composition wherein said at least one lipophilic active compound is at least one lipophilic veterinary drug, and wherein said polymeric matrix is not crosslinked and no covalent interaction occurs between the two or more polymers and between the polymers and the at least one lipophilic veterinary drug.

33. The veterinary composition according to claim 32, comprising a lipophilic veterinary drug selected from the group consisting of albendazole, fenbendazole and itraconazole.

34. The composition according to claim 1, which is a nutraceutical composition wherein said at least one lipophilic active compound is at least one lipophilic nutraceutical, and wherein said polymeric matrix is not crosslinked and no covalent interaction occurs between the two or more polymers and between the polymers and the at least one lipophilic nutraceutical.

35. The nutraceutical composition according to claim 34, comprising resveratrol or hesperetin as the lipophilic nutraceutical.

36. The nutraceutical composition according to claim 35, comprising resveratrol and two polymers forming the polymeric matrix, wherein one of the polymers is an amphiphilic polymer and the other is a hydrophilic polymer.

37. The nutraceutical composition according to claim 36, wherein the amphiphilic polymer is Poloxamer 407 and the hydrophilic polymer is sodium carboxymethylcellulose, sodium alginate or chitosan.

38. The pharmaceutical composition according to claim 11, comprising two lipophilic drugs.

39. The pharmaceutical composition according to claim 38, wherein the two lipophilic drugs are fenofibrate and atorvastatin.

40. The pharmaceutical composition according to claim 39, wherein both the fenofibrate and the atorvastatin are interwoven with the polymeric matrix of two or more polymers.

41. The pharmaceutical composition according to claim 40, wherein the polymeric matrix is formed by two polymers, one of the polymers is an amphiphilic polymer and the other polymer is a hydrophilic polymer.

42. The pharmaceutical composition according to claim 41, wherein the amphiphilic polymer is Poloxamer 407 and the hydrophilic polymer is sodium carboxymethylcellulose, sodium alginate or chitosan.

43. The pharmaceutical composition according to claim 11, further comprising one or more pharmaceutically acceptable carriers, excipients or both.

44. The pharmaceutical composition according to claim 43, formulated into a tablet.

45. The pharmaceutical composition according to claim 43, comprising an additional drug in combination with the composition comprising the lipophilic drug, wherein the additional drug is not interwoven with the polymeric matrix.

46. The pharmaceutical composition according to claim 45, wherein the lipophilic drug is fenofibrate and the additional drug is aspirin, and only the fenofibrate is interwoven with a polymeric matrix of two polymers.

47. The pharmaceutical composition according to claim 46, prepared by blending a composition comprising fenofibrate interwoven with a polymeric matrix of Poloxamer 407 and sodium carboxymethylcellulose, with aspirin, and formulating in capsules or tablets.

48. The veterinary composition according to claim 32, further comprising one or more veterinarily acceptable carriers, excipients or both.

49. The nutraceutical composition according to claim 34, further comprising one or more nutraceuticals, nutritional agents, acceptable carriers, excipients or a mixture thereof.

50. A method for the preparation of a solid composition according to claim 1, comprising the steps of:
 (i) preparing a clear and homogeneous solution of the two or more polymers and the at least one lipophilic active compound in a mixture of water and an organic solvent;
 (ii) drying the polymers-lipophilic active compound complex clear and homogeneous solution of (i) to form a solid composition; and
 (iii) formulating into said dosage form.

51. The method according to claim 50, wherein the aqueous solution has at least 50% by weight of water.

52. The method according to claim 50, wherein the drying in step (ii) is carried out by spray drying.

53. The method according to claim 50, wherein the polymers-lipophilic active compound clear and homogeneous aqueous solution is prepared by adding a solution of the lipophilic active compound in an organic solvent or in a mixture of water and an organic solvent to a homogeneous water or water-organic solvent solution of the polymers, and said organic solvent is selected from the group consisting of acetic acid, acetonitrile, acetone, 1-butanol, 2-butanol, N,N-dimethyl-acetamide; N,N-dimethylformamide, dimethyl sulfoxide, 1,4-dioxane, ethanol, formic acid, methanol, 3-methyl-1-butanol, methylethyl ketone, 2-methyl-1-propanol, 1-methyl-2-pyrrolidone, 1-pentanol, 1-propanol, 2-propanol and tetrahydrofuran.

54. The method according to claim 50, wherein the polymers-lipophilic active compound clear and homogeneous solution is prepared by adding a solution of the lipophilic active compound and amphiphilic polymers in an organic solvent or in a mixture of an organic solvent and water to a homogeneous water or water-organic solvent solution of the hydrophilic polymers, and said organic solvent is selected from the group consisting of acetic acid, acetonitrile, acetone, 1-butanol, 2-butanol, N,N-dimethylacetamide; N,N-dimethylformamide, dimethyl sulfoxide, 1,4-dioxane, ethanol, formic acid, methanol, 3-methyl-1-butanol, methylethyl ketone, 2-methyl-1-propanol, 1-methyl-2-pyrrolidone, 1-pentanol, 1-propanol, 2-propanol and tetrahydrofuran.

55. The method according to claim 53, wherein the lipophilic active compound is fenofibrate and the polymers-fenofibrate clear and homogeneous solution is prepared by adding a solution of fenofibrate in said organic solvent to a homogeneous water solution of the polymers.

56. The method according to claim 55, wherein a solution of fenofibrate in n-propanol is added to a water solution of the polymers Poloxamer 407 and sodium carboxymethylcellulose.

57. The method according to claim 55, wherein the polymers-fenofibrate clear and homogeneous solution is obtained by preparing a solution of fenofibrate in said organic solvent, adding the amphiphilic polymer and optionally water to the fenofibrate organic solution, and then adding the fenofibrate-amphiphilic polymer solution to the aqueous organic solvent solution of a hydrophilic polymer.

58. The method according to claim 55, comprising preparing a solution of fenofibrate in n-propanol, adding Poloxamer 407 and water to the fenofibrate n-propanol solution, and then adding the fenofibrate-Poloxamer 407 solution to an aqueous n-propanol solution of sodium alginate.

59. The method according to claim 55, wherein the polymers-fenofibrate clear and homogeneous solution is prepared by adding wheat gluten hydrolysate to a water solution of sodium carboxymethylcellulose, adding thereto polyvinylpyrrolidone and n-propanol under heating, and adding a solution of fenofibrate in n-propanol to the hot polymers solution under stirring.

60. The method according to claim 53, wherein a solution of atorvastatin in n-propanol is added to a water solution of the polymers Poloxamer 407 and sodium carboxymethylcellulose.

61. The method according to claim 53, wherein a solution of itraconazole in acetonitrile is added to a water solution of the polymers Poloxamer 407 and sodium carboxymethylcellulose.

62. The method according to claim 50, wherein the polymers-lipophilic drug clear and homogeneous solution is obtained by preparing a solution of the lipophilic drug in an organic solvent, adding the amphiphilic polymer and optionally water to the lipophilic drug organic solution, and then adding the lipophilic drug-amphiphilic polymer solution to an aqueous organic solvent solution of a hydrophilic polymer, and said organic solvent is selected from the group consisting of acetic acid, acetonitrile, acetone, 1-butanol, 2-butanol, N,N-dimethylacetamide; N,N-dimethylformamide, dimethyl sulfoxide, 1,4-dioxane, ethanol, formic acid, methanol, 3-methyl-1-butanol, methylethyl ketone, 2-methyl-1-propanol, 1-methyl-2-pyrrolidone, 1-pentanol, n-propanol, 2-propanol and tetrahydrofuran.

63. The method according to claim 62, comprising preparing a solution of atorvastatin in n-propanol, adding Poloxamer 407 and water to the atorvastatin n-propanol solution, and then adding the atorvastatin-Poloxamer 407 solution to an aqueous n-propanol solution of sodium alginate.

64. The method according to claim 62, comprising preparing a solution of itraconazole in n-propanol, adding Poloxamer 407 and water to the itraconazole n-propanol solution, and then adding the itraconazole-Poloxamer 407 solution to an aqueous n-propanol solution of chitosan HCl.

65. A clear and homogeneous solution comprising two or more polymers and a lipophilic active compound in an aqueous solvent in single phase that does not undergo sedimentation or precipitation, wherein at least one of the two or more polymers is an amphiphilic polymer and at least another of the two or more polymers is either a hydrophilic polymer or an amphiphilic polymer with a hydrophobic-hydrophilic balance different from the first amphiphilic polymer.

66. The composition according to claim 65, wherein the aqueous solvent consist of at least 50% by weight water and less than 50% by weight organic solvent, and the organic solvent is preferably selected from the group consisting of acetic acid, acetonitrile, acetone, 1-butanol, 2-butanol, N,N-dimethylacetamide; N,N-dimethylformamide, dimethyl sulfoxide, 1,4-dioxane, ethanol, formic acid, methanol, 3-methyl-1-butanol, methylethyl ketone, 2-methyl-1-propanol, 1-methyl-2-pyrrolidone, 1-pentanol, n-propanol, 2-propanol and tetrahydrofuran.

67. The composition according to claim 1, wherein said composition forms a colloidal nanodispersion upon contact with aqueous media.

68. The pharmaceutical composition according to claim 11, which is designed for release of the lipophilic active compound which is a lipophilic drug either in the gut or in the intestine.

69. The pharmaceutical composition according to claim 31, wherein the amphiphilic polymer is Poloxamer 407 and the hydrophilic polymer is sodium carboxymethyl cellulose.

70. The pharmaceutical composition according to claim 68, wherein said composition is designed for release of the lipophilic active drug upon contact with biological fluids with pH6-8 that corresponds to the pH of intestinal fluids.

71. The composition according to claim 1, wherein said composition forms a colloidal dispersion upon contact with aqueous media.

72. The composition according to claim 67, which is stable for at least 12 months when stored at 25° C. and 60% RH and does not exhibit any changes in the chemical or physico-chemical properties represented by the formation of colloidal nanodispersion upon contact with aqueous media, decreased enthalpy of melting, and decreased temperature of melting as the initial composition.

* * * * *